(12) United States Patent
McCabe et al.

(10) Patent No.: US 7,691,626 B2
(45) Date of Patent: Apr. 6, 2010

(54) SELF-CONTAINED CELL CULTURE APPARATUS AND METHOD OF USE

(75) Inventors: Edward R. B. McCabe, Pacific Palisades, CA (US); Urvashi Bhardwaj, Los Angeles, CA (US); Zakir Rangwala, Palos Verdes Estates, CA (US); Yao Hua Zhang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 356 days.

(21) Appl. No.: 10/579,952

(22) PCT Filed: Nov. 22, 2004

(86) PCT No.: PCT/US2004/039314

§ 371 (c)(1),
(2), (4) Date: May 22, 2006

(87) PCT Pub. No.: WO2005/069766

PCT Pub. Date: Aug. 4, 2005

(65) Prior Publication Data

US 2007/0082398 A1    Apr. 12, 2007

Related U.S. Application Data

(60) Provisional application No. 60/523,975, filed on Nov. 21, 2003.

(51) Int. Cl.
*A01N 1/00* (2006.01)
*A01N 1/02* (2006.01)
*C12M 1/00* (2006.01)
*C12M 3/00* (2006.01)

(52) U.S. Cl. .............. 435/307.1; 435/1.1; 435/1.2; 435/1.3; 435/373; 435/305.1; 435/305.2; 435/260; 62/3.3; 62/371; 62/62; 62/64

(58) Field of Classification Search .............. 435/307.1, 435/1.1, 1.2, 1.3, 373, 305.1, 305.2, 260; 62/3.3, 371, 62, 64
See application file for complete search history.

(56) References Cited

U.S. PATENT DOCUMENTS 4,306,556 A * 12/1981 Zelman .................. 604/410

(Continued)

FOREIGN PATENT DOCUMENTS

WO    WO 02/50251 A2 *  6/2002

OTHER PUBLICATIONS

Chaplen and Cameron, Anal. Biochem. (1996) 238:171-178.

(Continued)

*Primary Examiner*—William H Beisner
*Assistant Examiner*—Nathan A Bowers
(74) *Attorney, Agent, or Firm*—Morrison & Foerster LLP

(57) ABSTRACT

A self-contained cell culture apparatus and method of use in which a cell culture may be stored frozen for an extended period, then thawed, incubated and grown in a closed system without additional processing or added constituents. The apparatus and method readily lend themselves to automated handling and analysis by MEMS devices, and find particular application in micro gravity and/or high radiation environments. It is emphasized that this abstract is provided to comply with the rules requiring an abstract that will allow a searcher or other reader to quickly ascertain the subject matter of the technical disclosure. It is submitted with the understanding that it will not be used to interpret or limit the scope of the claims.

23 Claims, 10 Drawing Sheets

U.S. PATENT DOCUMENTS

| | | | | |
|---|---|---|---|---|
| 4,865,871 A | * | 9/1989 | Livesey et al. | 435/1.3 |
| 5,209,745 A | * | 5/1993 | Irr et al. | 604/415 |
| 5,679,565 A | | 10/1997 | Mullen et al. | |
| 5,693,537 A | * | 12/1997 | Wilson et al. | 435/401 |
| 5,827,741 A | | 10/1998 | Beattie et al. | |
| 5,843,766 A | * | 12/1998 | Applegate et al. | 435/284.1 |
| 5,863,715 A | | 1/1999 | Rajotte et al. | |
| 5,964,261 A | | 10/1999 | Neuenfeldt et al. | |
| 6,065,294 A | * | 5/2000 | Hammerstedt et al. | 62/3.3 |
| 6,068,775 A | * | 5/2000 | Custer et al. | 210/638 |
| 2002/0168759 A1 | * | 11/2002 | Wang et al. | 435/307.1 |
| 2006/0246490 A1 | * | 11/2006 | Anderson et al. | 435/6 |

OTHER PUBLICATIONS

International Search Report for PCT/US04/39314, mailed on Jan. 25, 2006, 3 pages.

Jovov et al., Am. J. Physiol. (1991) 261:C1196-203.

Kostov et al., Biotechnology and Bioengineering (2001) 72:346-352.

Lakey et al., Transplantation (2001) 72(6):1005-1011.

NASA, Annual Report (2003) NASA Physical Science Research Division, pp. 1-132.

Naughton, Ann. N.Y. Acad. Sci. (2002) 961:372-385.

Sannino et al., Journal of Applied Polymer Science (2004) 91:3791-3796.

Sannino et al., Journal of Biomedical Materials Research Part A (2003) 67A:1016-1024.

Weigl et al., Journal of Biotechnology (1994) 32:127-138.

* cited by examiner

SELF-CONTAINED CELL CULTURE APPARATUS AND METHOD OF USE

CROSS-REFERENCE TO RELATED APPLICATIONS

This application is the national stage of PCT application PCT/US2004/039314 having an international filing date of 22 Nov. 2004, which claims priority from U.S. provisional application Ser. No. 60/523,975, filed 21 Nov. 2003. The contents of these documents are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract/Grant No. NCC2-1364 awarded by the Center for Cell Mimetic Space Exploration (CMISE).

TECHNICAL FIELD

The present invention relates to cell culture in a sealed completely self-contained system which may be stored frozen. When required, the cell culture may be thawed and incubated in an appropriate liquid media in the presence of a predetermined atmosphere, all of which are contained within the sealed apparatus. The apparatus may be exposed to any type of environmental factors (chemical; toxic or nontoxic, biological; such as viruses for example, but not cell culture contaminants) under study, and may be coupled with instrumentation to detect and measure selected molecules and physical parameters within the apparatus. The use of any cell type, prokaryotic or eukaryotic, listed in the collection of any cell repository or any cell type in an individual's collection(s) or freshly isolated from tissue is considered to be within the scope of the present invention.

BACKGROUND ART

The in vitro cultivation or culturing of eukaryotic cells is well known. Presently, repositories for cell cultures world wide contain more than 5,000 different eukaryotic cell types which may be grown in vitro in appropriately selected liquid media. The European Collection of Cell Cultures (ECACC), for example, maintains cultures of more than 50 cell types from over 40 species. Many other eukaryotic cell lines available to investigators are listed in the catalogues of the ATCC American Type Culture Collection, DCTDC Tumor Repository, DSMZ Human and Animal Cell Cultures, ICLC Interlab Cell Line Collection, Istituto Giannina Gaslini, IZSBS Istituto Zooprofilattico Sperimentale and NIA National Institute of Aging Cell Repository.

Cell culture is a powerful approach originated over a century ago to study the behavior of different cells under physiological conditions as well as stress. In vitro cell culture is greatly influenced by an environment that favors the spreading, migration and proliferation of cells. The cell culture environment includes: the nature of the substrate or phase on or in which cells grow that may be a solid surface, as in monolayer growth, or a liquid, as in a suspension culture; the physiochemical and physiological composition of the medium; the constitution of gas phase; and the incubation environment, including temperature and humidity. A wide variety of liquid media suitable for the maintenance and growth of mammalian cells for in vitro culture have been formulated and are commercially available.

Conventional cell culture cannot be performed in the absence of a cell culture facility staffed by well-trained and experienced personnel. In addition, conventional methods require removal of a cryoprotectant from cryopreserved cells upon cell revival. This removal of cryoprotectant (e.g., DMSO, glycerol) from cryopreserved cells involve multiple. steps and is usually performed by an experienced personnel. As soon as cryopreserved cells ate thawed 37° C., they are carefully transferred drop wise into a 10 ml centrifuge tube containing Hanks balanced salt solution or phosphate buffered saline. This gradual dilution process is particularly important when DMSO is used as the cryoprotectant, with which sudden dilution can cause severe osmotic damage and reduce cell survival. The 10 ml tube containing cells is centrifuged at 230 g for 4:30 minutes. The DMSO in the supernatant is aspirated and the cells are recovered and transferred to the cell culture flask in the presence of prewarmed growth medium which is conventionally prewarmed at 37° C. for 15 minutes prior to cell culture. The cell culture flask is kept at 37° C. in a $CO_2$ incubator, and cell growth and viability are observed. Therefore, it would be useful to the industry to have a system for performing cell culture that does not require well-trained and experienced personnel.

Further, it would be advantageous to perform cell cultures without the need to remove cryoprotectant upon cell revival. Therefore, due to the enormous applicability and utility of cell culture in biology, it is desirable to have a self-contained system capable of performing cell culture without human manipulation. The present invention addresses these needs by providing a completely self-contained cell culture system that can be stored for extended periods of time. When required, this system may be thawed and incubated at the desired temperature to carry out cell culture without the need to remove the cryoprotectant.

DISCLOSURE OF THE INVENTION

The present invention is directed to a cell culture apparatus or vessel, a self-contained cell culture system or kit, and components that may be used with the vessel or kit, namely reservoirs that may be filled with gas, media, or cell culture which are useful in methods of the invention. In one surprising aspect of the methods of the invention, cells may be grown in the presence of a cryoprotectant as long as the cells are diluted in growth media such that cell viability is maintained. Such effort allows for each of the vessel's uses, as cryoprotectant need not be removed from the cell culture, as in conventional methods, in order to revive cells using the inventive vessel.

One embodiment of the invention is a method for growing cells, comprising reviving cells for culturing in the presence of a cryoprotectant, wherein the cells are diluted in a growth medium such that cell viability is maintained. Preferably, the cryoprotectant is DMSO, and more preferably, DMSO is present in an amount of less than 2% by volume based on total volume of cells and media present. Even more preferably, the cells are grown in a self-contained cell culture vessel.

Another embodiment of the invention is a kit comprising a self-contained cell culture vessel, cells and a cryoprotectant disposed in a cell reservoir, a liquid cell culture media disposed in an internal chamber of the vessel or in a media reservoir of an amount capable of diluting the cryoprotectant to a volume suitable for cell growth, and gas disposed in the gas reservoir.

In one embodiment, the kit is maintained at a subzero temperature.

Another embodiment of the invention is directed to a method for growing cells in a self-contained cell culture vessel at a temperature suitable for cell culturing comprising incubating the kit described herein.

Another embodiment of the kit contains a cell culture vessel comprising the internal chamber defines a space therein and has an internal surface, defines at least one optional sealable port or channel, and defines at least one sealable opening for receiving a gas reservoir capable of fluid communication with the internal chamber. The gas reservoir may either contain a valve or removable seal defined between the gas reservoir and the internal chamber or itself be a self-contained reservoir that is capable of being disposed of within the internal chamber. The cell reservoir is capable of fluid communication with the internal chamber and defines an optional valve therebetween. The media reservoir is capable of fluid communication with the internal chamber and defines an optional valve therebetween. The vessel is capable of being sealed, and is made from a material capable of withstanding subzero temperatures without degrading.

In another embodiment, the vessel further comprises a liquid impermeable flexible partition having two sides displaced within the internal chamber. The partition is capable of exchanging gas between said first and second space. The first side defines a first space for containing a liquid which is in communication with at least one port or channel and defines a sealable access port. The second side defines a second space for containing a gas which is capable of fluid communication with the gas reservoir. The edges of the partition are sealed to a portion of the internal surface of the internal chamber to prevent liquid communication between said spaces.

In another embodiment, the vessel further comprises a fluid impermeable expandable wall affixed to a rigid wall of the internal chamber and forming an integral portion of the internal chamber. The fluid impermeable expandable wall and the partition define the gas space.

In another embodiment, the valve or seal described above is capable of opening and closing. Preferably, at least one port or channel sealably connects to at least one media chamber through at least one fluid channel, wherein at least one valve or seal is displaced between each port or channel and each media chamber. Further, at least one port or channel also sealably connects to at least one absorbent chamber wherein at least one valve or seal is displaced between each additional port or channel and the absorbent chamber. This embodiment also comprises a cell filter proximal to each valve or seal and between each valve and seal and each absorbent chamber.

In another embodiment, the gas reservoir is a self-contained capsule disposed within the internal chamber or is disposed outside the internal chamber.

In another embodiment, the cell reservoir and the media reservoir are present in the internal chamber, preferably where the cell reservoir and/or the media reservoir is a self-contained capsule.

In another embodiment, the seal or valve defined between the gas reservoir and the internal chamber described above is selected from the group consisting of a) a temperature sensitive plug; b) a diaphragm adapted to be penetrated, or c) a mechanically, thermally or electrically operated valve. In a further embodiment, a safety seal is present in addition to the temperature sensitive plug. Preferably, the internal chamber of the vessel is removably or fixedly connected to at least one measuring device via at least one port or channel, such as at least one Micro Electro Mechanical System (MEMS) and/or high performance liquid chromatograph (HPLC).

In one embodiment, at least one port or channel defines at least one mechanism to provide fluid communication between the internal chamber and the measuring device, such as a ball valve or perforable diaphragm. Preferably, the internal chamber defines one or two ports or channels.

In a further embodiment, the measuring device comprises a member for operating the ball valve or for penetrating the diaphragm. Preferably, the port or channel has a filter for preventing contamination in the internal chamber.

In one embodiment, the sealable access port is removably sealed with an access port closure.

In another embodiment, the kit further comprises at least one sensor externally connected to at least one port or channel or disposed inside the internal chamber, e.g., for sensing oxygen, CO2, or pH levels.

An additional embodiment of the invention is a method to transport cells from a distribution site to a site where a transplant takes place, comprising transporting the kit at a temperature suitable for maintaining cell viability to a site where the cell transplant takes place; and reviving said cells, such as islet cells, in said vessel at a transplant site.

MODE FOR CARRYING OUT THE INVENTION

Figure 1:
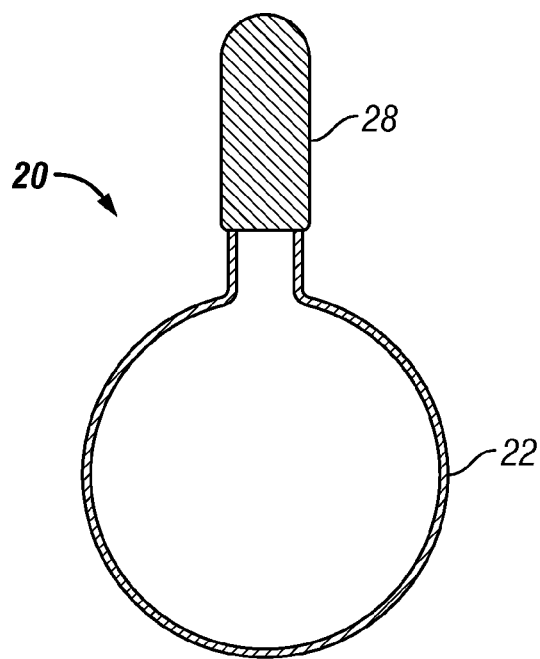
FIG. 1 is a top view of an embodiment of the present invention.

The vessel comprises in its most basic aspect an internal chamber and a gas reservoir. The internal chamber may optionally contain at least one sealable port or channel. Such port or channel is useful for sealably and/or removably connecting additional reservoirs, such as those for media or gas, measuring devices such as MEMS or HPLC, chambers such as those for media or absorbent material, or sensors such as those that sense oxygen or pH levels.

The extra media and gas compartments will function as additional media/gas carriers, which can be injected into the main compartment to extend the viability of the cells in the culture. There can be more than one extra media/gases compartment, each individually separated from the main by a valve or membrane that can be activated to open and infuse fresh content into the main compartment as needed. The material for this compartment must be biocompatible, sterilizable, and inexpensive. An example of such material is the plastic polyvinyl chloride (PVC or vinyl), which has been used safely in medial devices for more than 40 years. It is typically rigid but can be made flexible using plasticizers such as phthalate esters. It has been used for bags to store both intravenous fluid as well as blood.

The vessel refers to the cell culture apparatus. The cell culture apparatus (20) of the present invention is preferably made of polymeric materials suitable for the maintenance and growth of cell cultures, and is of a rugged and durable construction so as to be reliably operable following exposure to conditions such as prolonged low temperature, low pressure, high acceleration, microgravity, zero gravity, mechanical vibration and/or shock.

Preferably, the internal chamber has at least one sealable opening. This sealable opening may be used to receive the gas reservoir, and may also be used to receive cell culture or media or reservoirs containing them.

The gas reservoir may be an independent reservoir such as a capsule that can be placed in the internal chamber of the vessel or it may be attached to the internal chamber, for example, via the sealable opening. The gas reservoir may contain a valve or removable seal such that gas contained in the gas reservoir may leave through the valve or removable seal to the internal chamber. Alternatively, the gas reservoir may be a self-contained reservoir such as a capsule.

In a preferred embodiment, the cell culture vessel or apparatus may also contain a cell reservoir or a media reservoir. Similar to the gas reservoir, the cell reservoir and the media reservoir may be a self-contained reservoir such as a capsule. In addition, the media may simply be contained in the internal chamber. Although the cell and media reservoirs may be disposed outside of the internal chamber, it is preferred that they are on the inside thereof.

The gas, or cell, or media reservoirs may simply be a capsule, for example a gelatin capsule that is capable of containing each of the gas, media, or cell culture components. Such reservoirs, preferably capsules, are preferably designed to maintain their structural integrity at subzero temperatures, but should liquefy or dissolve at temperatures suitable for cell growth. In another aspect, such reservoirs contain at least one opening housing a plug that prevents the content of the reservoirs from being released at subzero temperatures, but allows for the release of the reservoirs' contents at temperatures suitable for cell growth.

Subzero temperatures refer to temperatures at which cell culture may be frozen or cryogenically prepared for revival. Preferably, subzero temperatures are less than −50° C., but dry ice temperatures of about −70° C. to −80° C. are also preferred, such as for relatively short term (about six months) of preservation, and more preferably less than −100° C., −120° C., −140° C., or lower, especially for preservation greater than one year. Preferably, transporting cells takes place at temperatures of −80° C., but may also occur at −20° C. and temperatures approximately 0° C., such as less than or equal to 4° C.

Temperatures suitable for cell growth are those temperatures at which cells from cryogenic preservation may be incubated and revived. The optimal temperature of cell culture is dependent on the body temperature of the source (animal or plant), and any anatomical variation in the temperature. Such temperature range is preferably from about 25° C. to 37° C., although any appropriate temperature is contemplated (e.g., 15° C. to 38.5° C.).

The internal chamber may be of various sizes. In one aspect, an industrial scale vessel is contemplated which may contain many liters of cell culture and media. However, very small scale internal chambers are contemplated that will allow for incubation of small quantities of cells or single cells. Such chambers may have a volume of 1-1,000 μL. Preferably, the volume of the internal chamber is about 2-500 μL, more preferably 50-300 μL. Single cells may be incubated in an internal chamber having a volume of 100 μL or less.

The vessel or apparatus may have a liquid impermeable but gas permeable flexible partition which is capable of segregating the liquid from the side of the partition that contains the gas. The partition may be made out of materials similarly suitable for prolonged low temperature, low pressure, high acceleration, microgravity, zero gravity, mechanical vibration and/or shock. For example, the partition may be made of a material, or a material having a coating, of polytetrafluoroethylene (PTFE) which allows for gas to flow through, but not liquids. An example of such material is known as Gore-Tex®. A silicone membrane may also be used as a partition.

In another embodiment, a portion of the internal chamber's wall is made up of a fluid impermeable expandable wall which is biocompatible. Examples of such an expandable wall are fluorosilicone rubber and LoPerm, which is a low-permeation fluorosilicone rubber. The expandable wall may be flexible or inflexible, but preferably flexible, such as a membrane. Such a membrane may act as a bladder which can inflate if the volume inside the internal chamber may need to increase, for example, if the temperature of gas is raised. The internal chamber will appear non-inflated, for example, when freezing and stored, but upon thawing and incubation for cell culture the membrane, or bladder may expand.

In one aspect, the vessel along with the gas, the media, and the cell culture, may be provided as a kit. Such self-contained kit will allow individuals with little experience to thaw and incubate the cell culture contained in such kit. Such kits will also enable cell retrieval and incubation without first removing the cryoprotectant.

In addition, in another aspect of the invention, reservoirs may be prepared for use in a vessel, for example, to replace the gas, media, and/or cell culture reservoirs used. Such reservoirs may be provided frozen so that a technician may simply add them to a vessel, in the appropriate space if, for example, a partition is present, and then the reservoirs may be warmed and incubated to grow the cells.

It is not necessary to remove the cryoprotectant from the cell culture upon thawing and reviving the cells if the cells are sufficiently diluted in the media. Preferably, the cryoprotectant, such as DMSO, must be less than 2% by volume of the volume of the final culture media (i.e., the cells, the cryoprotectant containing media, and the growth media). For example, 1 mL of a frozen specimen containing approximately 5 to 10% of cryoprotectant by volume may be diluted with 3.5 mL to 15 mL of media by volume. For example, about 7.5% of DMSO in the cryoprotectant medium which contains the cells and the growth media may be diluted with media to a final concentration of about 2.0% to 0.4% by volume of the cells, cryoprotectant media and growth media.

Typical cryoprotectants include glycerol or dimethylsulfoxide (DMSO) or other cryoprotectants known in the art, such as propan-1,2,-diol and butan-2,3-diol. In a preferred embodiment, the DMSO-based medium is prepared by diluting 15% based on DMSO (dimethylsulfoxide) in Basal Eagle's Medium with Hanks' BSS (Basal Salt Solution) (Cat. No. 12-132A, BioWhittaker, Walkersville, Md.) diluted 1:1 with culture medium appropriate for cell type, e.g., RPMI 1640 containing 10-20% FBS for EBV transformed lymphoblastoid cell lines (LCLs) or Dulbecco's Modified Eagle's Medium for fibroblasts. In another embodiment, the Glycerol-based medium is prepared by diluting 50% Glycerol in the cell-type-appropriate medium with a volume of the same cell-type-appropriate medium to a final concentration of 15-20% Glycerol.

Typically DMSO is used as cryoprotectant, however, depending on the cell type, other cryoprotectants can also be used. A cryoprotectant should be used at a concentration to avoid ice formation, and it should be minimally toxic in order to maintain cell viability at subzero temperature. The range of concentration of cryoprotectant that maintains cell viability can be established by using the standard protocol of live/dead cell staining. Trypan blue is the most common stain used to distinguish viable cells from nonviable cells. It stains nonviable (dead) cells. However, it is time sensitive. The standard steps for this protocol are:

1. Dilution of cell suspension 1:5 in 0.4% Trypan blue
2. Loading small amount of this preparation on the hemocytometer and cells are counted under inverted microscope.
3. The percentage of viability is calculated thus:
    a. % viability=(# viable cells counted)/(total # of cells counted)×100
4. Dependent on the application of the self-contained apparatus, the minimum concentration (needed to reach by dilution) of the cryoprotectant is defined by the acceptable viability percentage upon cell revival, typically 40%-50%.

One use of the self-contained vessel described above involves its use in the transplantation of cells that are stored in the vessel. Conventionally, a physician or surgeon removes cells from a donor. For example, a surgeon may remove a pancreas from a deceased donor. Then a tissue culture specialist isolates cells, if necessary; for example, islet cells may be isolated from a pancreas. The isolated cells are delivered at room temperature to a transplant site and, thereafter, a surgeon, after appropriate preparation, transplants the cells to a recipient at a recipient transplant site. According to conventional methods, the transplant must be performed in less than 12 hours. A problem arises in finding a matching recipient within this time frame. Also, due to the time constraints, the extraction, isolation, and preparation (e.g., for islet cells) must be highly efficient for the recipient to receive sufficient cells. Conventional techniques require two donors for a single recipient. Such time constraints also geographically hinder the ability of these cells or transplant material to reach the recipient. Even in cases where cells are frozen after the processing steps (i. e., not as a part of the inventive apparatus), conventional shipment is performed in dry ice and the recipient transplant site will need to have the required resources such as personnel and the facility to thaw and culture the frozen cells.

Such constraints with respect to storage and transport described above are avoided by transporting cells in the inventive vessel described herein. For example, a surgeon or specialist may remove cells from an autologous, syngeneic, allogeneic, or heterologous source, such as a pancreas from the deceased donor. A tissue culture specialist may then process the cells to obtain a homogeneous or heterogeneous population of cells with a particular or set of desirable characteristics or functions. For example, in a preferred embodiment, islet cells are isolated from a pancreas. The cells may be added, with a cryoprotectant, to the vessel that has been pre-charged with the appropriate media and gas. The cells may be frozen along with the pre-charged media and gas in the self-contained vessel and may be stored for an extended period of time. Personnel may then deliver the frozen cells in the self-contained vessel at temperatures such as −80° C., −20° C., or 40 C to a transplant site. Some specialized cells, such as stem cells, may not be able to tolerate temperature fluctuations from −80° C. to −20° C., so the temperature at which the cells are transported may vary based on the type of cells used. In one aspect, the transplant site may continue to store the frozen cells. In one aspect, the cells are delivered to a surgeon or technician, who revives the cells. For example, such revival may take place by placing the entire vessel, along with its frozen contents, under conditions of 37° C. The surgeon then may perform the transplant of the revived cells to a recipient, for example, at a recipient transplant site. In a preferred embodiment, islet cells are transplanted to a matching recipient.

The method of the invention using the vessel described herein eliminates the necessity of finding immediately a recipient in less than 12 hours, as the transplant material can be stored at the processing site or site where the recipient transplant takes place for more than two days, for example. Storage and cell activation merely requires, for example, a freezer which will maintain the cells function on thawing, such as at −80° C., and an incubator for reviving cells, such as at 37° C. Thus, more time is available to find a matching recipient. Also, geographical constraints will be removed, as the vessel can be shipped frozen and stored frozen at a donor surgery site or the recipient site.

Although the more detailed description of embodiments that follows describes a cell culture system and the experiment performed was on cell lines, the culture may be used to include culturing of both prokaryotic and eukaryotic cells (e.g., mammalians, such as human and non-human cells). The population of cells in the system being cultured can be homogeneous or heterogeneous. Furthermore, the organization of cells in the system can vary from cells to tissues to complex organs. Thus, the definition of "cells" includes cells, tissues, and organs. Examples of homogeneous group of cells include cell lines (e.g., lymphoblastoid cells, fibroblasts), and primary cells (e.g., adrenal cells, fibroblasts, stem cells (adult and embryonic)). Examples of heterogeneous group of cells include tissues and organs (e.g., islet).

There are some technical problems with using this system for embryonic stem (ES) cells. ES cells grow on a feeder layer of cells, which is grown for 24 hours before seeding ES cells. To solve this technical problem, feeder cells can be stored in a separate capsule and released with appropriate media and gas, 24 hrs before releasing ES cells. We tested this system on mouse ES cells. Feeder cells were grown for 24 hours followed by ES cells. We were able to successfully revive and grow ES cells in this system. These data indicate the capability of this system for many different cell lines by modifying the parameters.

As is known to one skilled in the art, cell culture in vitro requires a culture media formulated to the nutritional and metabolic requirements of the particular cell type to be cultured. For example, human lymphocytes freshly isolated from peripheral blood may be maintained and grown in RPMI 1640 liquid media supplemented with 10% to 20% fetal bovine serum (FBS) when in the presence of a mitogen, such as phytohemaglutinin or phorbal ester, or after viral transformation (EBV, SV40). It is also known to those skilled in the art that a variety of other cell types isolated directly from tissue may be suitable for maintenance and growth in in vitro culture following application of established techniques for isolation and growth stimulation as is conventional.

The self-contained environment for culture and storage for culture is general across most cells but specific parameters are required for specific cells and tissues (e.g., medium and atmosphere appropriate for specific cells and tissue). Each cell line, such as a mammalian cell line, needs an appropriate growth media (10% RPMI 1640 for lymphoblastoid cell lines and 10% DMEM for fibroblasts). Most of the cell lines require 5% $CO_2$ and 95% air; however, for some cell lines, 10% $CO_2$ and 90% air is used.

A wide variety of liquid media suitable for the maintenance and growth of eukaryotic cells in in vitro culture have been formulated and are commercially available from a number of suppliers. Such conventional cell culture media include completely defined media in which all constituents are known, such as for example, X-Vivo 20.® (Bio-Whittaker), Waymouth Medium (Sigma-Aldrich) and NCTC Medium (NCI), as well as media typically supplemented with serum, such as RPMI 1640 (Sigma-Aldrich), Dulbecco's MEM (Sigma-Aldrich) and Medium 199 (Sigma-Aldrich).

Growth media is stored frozen simultaneously along with the mammalian cells under subzero conditions without denaturing the constituents required for normal cell growth. This innovation eliminates the need of pre-warming of media for at least 15 minutes at temperature appropriate for cell growth, usually 37° C. prior to cell culture. The inventive self-contained cell culture apparatus capability or storing and culturing mammalian cells overcomes such disadvantages.

Thus, in a preferred embodiment, the present invention is directed to a completely self-contained cell culture system wherein a cell culture may be viably stored frozen for extended periods then incubated and grown when required utilizing only constituents within the self-contained system, and to an apparatus and method whereby this may be accomplished.

One aspect of the present invention provides an apparatus and method wherein a viable cell culture may be stored frozen, thawed, incubated and grown in a single vessel wherein the cell culture, media and atmosphere necessary thereto are within a completely self-contained device.

Another aspect of the present invention provides an apparatus and method wherein a cell culture may be stored frozen, thawed, incubated and grown in a self-contained system without the addition of any cell culture, media, atmosphere or other constituent or component from outside the system.

Another aspect of the present invention provides a cell culture apparatus adapted to maintain a viable cell culture for a predetermined minimum time period when stored at temperatures below minus 120° C.

Another aspect of the present invention provides an apparatus that can be thawed from below minus 120° C. to a temperature at which the cells are viable.

Another aspect of the present invention provides a cell culture apparatus adapted to maintain a viable cell culture for a predetermined time period when incubated at a temperature of approximately 37° C. or another temperature to which the cells are adapted naturally or artificially for growth.

Another aspect of the present invention provides a self-contained cell culture apparatus adapted to be functionally connected with instrumentation to measure or detect selected molecules in the cell culture media and/or to monitor physical parameters within the apparatus.

Another aspect of the present invention provides a self-contained cell culture apparatus that may be coupled with instrumentation permanently or as a separate module after thawing for detecting the presence of selected molecules released into the cell culture media and for measuring predetermined parameters associated with the selected molecules.

Another aspect of the present invention provides a self-contained cell culture apparatus adapted to be functionally connectedly a detecting and/or measuring instrument such as a MicroElectroMechanicalSystem (MEMS) device, high performance liquid chromatography, spectrometry (mass spectrometry, gas chromatography-mass spectrometry), gene chip, immunoassay or the like.

It will be understood by those of ordinary skill in the art that all embodiments of the apparatus are assembled under aseptic conditions using only sterile materials and supplies as is conventional in the art. There are several benefits of the vessel, kit, and methods of the invention. The self-contained cell culture system can be used for packaging, storage, transportation as well as culturing cells, particularly mammalian cells. This system can be used to transport cells in dry ice as well as at higher temperatures such as −20° C. This self-contained cell culture system eliminates the requirements for a highly trained tissue culture technician and a separate room for a tissue culture laboratory aseptic area, water bath, laminar flow hood or special cell culture incubator. One simply requires a freezer (e.g., −80° C. or lower) to store these containers, and an ordinary 37° C. temperature controlled environment (not requiring a water jacketed (and therefore very heavy) incubator with an integrated system providing $CO_2$ gas) to initiate cell culture. Since, this system is self-contained and can be used by individuals without experience or skill in cell culture, therefore it has the potential to be automated. The logistical innovations represented by this system will permit cell culture in settings in which, and by and for individuals for whom it would not have been available previously. The diagnostic and therapeutic applications of this innovation system are far-reaching.

In a well-established cell culture facility, using currently established protocols each cell culture costs ~$40. However, by using the self-contained apparatus, we estimate that the cost could be reduced to ~$3-4 as one would be able to perform cell culture in an ordinary 37° C. incubator without any specialized area, equipment or skilled personnel. This would therefore reduce the bulk and weight of the payload required for cell culture, for example in space, as well as the volume and equipment dedicated to this endeavor on Earth, planetary outposts and in space.

In addition to cost-benefit, the self-contained cell culture system has enormous potential applications for medicine, research, environmental health and safety, drug screening, and therapeutics.

Another aspect of the present invention provides a self-contained cell culture apparatus adapted for assessment of the effects of radiation or other external influences (e.g., environmental toxins, chemicals, drugs, growth factors, biological stress factors such as viruses, or the like) upon cells in culture.

Another aspect of the present invention provides a system for automated use by individuals without experience or skill in tissue culture such as by first responders in case of chemical poisoning, epidemic out-break due to deadly viruses, water quality assessment, industrial areas to determine the effect of chemicals on the risk of development of chronic conditions such as cancer, forensic studies, on field studies in remote areas, in hot zone P4 facilities, by individuals aboard spacecraft for assessment of space environmental factors such as radiation upon viable cells (preferably, but not limited to eukaryotic and preferably but not limited to mammalian) in culture.

The self-contained cell culture apparatus can be adapted to assess and monitor various environmental stimuli that can induce physiologically-relevant changes in cells. A clear example is the application of this apparatus for space exploration. Cells of astronauts who are preparing for duty at space can be isolated and cryopreserved using the self-contained cell culture apparatus. The apparatus packages the fragile cells in a robust, frozen state capable of enduring highly physical stress encountered during transport, such as the rocket launch to space. Because the self-contained cell culture apparatus does not require expert handling or the traditionally large culture facility, the cells in the apparatus can be revived in space by an automated system. Then, these revived cells can be used as physiological surrogates of the astronauts (a sentinel monitoring device) to predict the potential physiological impact of harmful space environment on the astronauts, such as continuous high dosage of radiation. The changes in the cells, e.g., fluctuation in the nitrous oxide (NO) production and specific gene pathway activations, caused by such environmental stimuli can be measured using standard cellular and chemical characterization techniques (e.g., electrochemical measurements and micro array assays for DNA, RNA or peptides) with measuring instrument attached to the apparatus, as described in embodiment 2 and 3, or in laboratories after the apparatus returns to Earth. Other applications using cells in self-contained cell cultures apparatus to monitor environmental threats and biological threats where such threats would present a danger to human involvement are simple extension of the previous example. Revived cell samples that were banked and stored in the self-contained apparatus can also be used to diagnose physiological response or to test drug response related to individuals or groups of individuals having similar cellular/genetic makeup. The basic process remains the same as the space application described above, where the revived cells in the self-contain apparatus is exposed to the stimuli of interest, and then measurement are made by attached measuring instrument or at common cell characterization laboratories.

Furthermore, cell culture system provides a method to store, transport, and distribute cells/tissues to be used in cell/tissue replacement therapy and related forms of regenerative medicine. This solution is extremely important since current cell/tissue therapy does not have a mechanism to transport cells from a distribution site to a site where the transplantion takes place. Further, this invention provides an easy solution to store these cells at the transplant site.

The components of preferred embodiments, discussed in detail hereinafter, are summarized in Tables 1-3 below.

TABLE 1

OUTSIDE COMPONENTS

| Components | Before Culture/During Cryopreservation | Upon Culture/Thawing |
|---|---|---|
| Cells (99) | Suspended in cryogenic protective media and housed within cell reservoir (30) | Enters internal chamber with cryogenic media |
| Cryogenic protective media (32) | Preserved with cells and housed within cell reservoir (30) | Enters into internal chamber with cells |
| Media (36) | Housed within media reservoir (34) | Enters into internal chamber; this is where pH/Oxygen detection can take place in the fourth embodiment |
| Gas (38) | Housed in gas reservoir (28) | Enters into internal chamber |

TABLE 2

EMBODIMENT 1

| Components in device | Description |
|---|---|
| A vessel (22) | Containing primarily of the following components:<br>1. an internal chamber;<br>2. a media reservoir (34)<br>3. a gas reservoir (28)<br>4. a cell reservoir (30) |
| An internal chamber (24) | Part of the vessel where gas from the gas reservoir, media from the media reservoir, and cells from the cell reservoir will be released into. |
| Surface on internal chamber (26) | This is where cells can attached if they are not grown in suspension. |
| A media reservoir (34) | Part of the vessel; can be inside of internal chamber or can be optional. |
| A valve/seal between media reservoir and internal chamber (Optional) | Enables fluid communication between media reservoir internal chamber when it opens. |
| A cell reservoir (30) | Part of the vessel; can be inside of internal chamber or can be optional. |
| A valve/seal between cell reservoir and internal chamber (Optional) | Enables fluid communication between cell reservoir and internal chamber when it opens |
| A gas reservoir (28) | Part of the vessel; it can be inside internal chamber or outside internal chamber |
| A valve/seal between gas reservoir and internal chamber (42) | Enables fluid communication between gas reservoir and internal chamber when it opens |
| A safety seal in gas reservoir (Optional) | |

TABLE 2-continued

EMBODIMENT 1

| Components in device | Description |
| --- | --- |
| A port/channel (46) | Enables fluid communication between internal chamber with MEMS device |
| A second port/channel (56) | Enables fluid communication between internal chamber with MEMS device and additional media or any other fluid reservoir |
| A MEMS device/HPLC | Connected to the apparatus by:<br>a. integrated<br>b. affixed<br>c. mated |
| A ball valve/a perforable diaphragm (Optional); it is present only if the MEMS device is mated with apparatus instead of being integrated with or affixed to the apparatus) | |
| A member which operates the ball valve or which penetrates the diaphragm (Optional) present if the MEMS device is mated with apparatus instead of being integrated with or affixed to the apparatus) | Part of the MEMS structure |

TABLE 3

EMBODIMENTS 2 AND 3

| Components with device | Description |
| --- | --- |
| A vessel (22) | Containing primarily of the following components:<br>1. an internal chamber;<br>2. a media reservoir<br>3. a gas reservoir<br>4. a cell reservoir |
| An internal chamber (24) | Part of the vessel where cells, media, and gas will be released from the gas reservoir (28), media reservoir (34), and cell reservoir (30) upon culture. |
| Surface on internal chamber (26) | This is where cells can attached if they are not grown in suspension. |
| *A liquid space (54) | Part of the vessel and within the internal chamber; this is in fluid communication with media reservoir and cell reservoir |
| A media reservoir (34) | Part of the vessel; can be inside of internal chamber or can be optional; this is in fluid communication with liquid space |
| A valve/seal between media reservoir and internal chamber (Optional) | Enables fluid communication between media reservoir and liquid space in internal chamber when it opens |
| A cell reservoir (30) | Part of the vessel; can be inside of internal chamber or can be optional; this is in fluid communication with liquid space |
| A valve/seal between cell reservoir and internal chamber (Optional) | Enables fluid communication between cell reservoir with liquid space in internal chamber when it opens |
| A gas reservoir (28) | Part of the vessel; it can be inside internal chamber (specifically, inside gas space) or outside internal chamber; |
| *A gas space (52) | Part of the vessel and within the internal chamber; in gas communication with liquid space. |
| A valve/seal between gas reservoir and gas space in internal chamber (42) | Enables fluid communication between gas reservoir with gas space in internal chamber when it opens |
| *A liquid impermeable and gas permeable flexible partition between gas space and liquid space (50) | |
| *A partition wall (40) | Affixed to by partition |
| *An access port (44) | |
| *An access port closure (58) | Closes access port until opened manually |
| A safety seal in gas reservoir - optional | |
| A port/channel (46) | Enables fluid communication between liquid space within internal chamber and MEMS device |
| A second port/channel (56) | Enables fluid communication between liquid space within internal chamber and MEMS device |

TABLE 3-continued

EMBODIMENTS 2 AND 3

| Components with device | Description |
|---|---|
| A MEMS device/HPLC (48) | |
| A ball valve/a perforable diaphragm (Optional); it is present only if the MEMS device is mated with apparatus instead of being integrated with or affixed to the apparatus) | |
| A member which operates the ball valve or which penetrates the diaphragm (Optional) present if the MEMS device is mated with apparatus instead of being integrated with or affixed to the apparatus) | Part of the MEMS structure |
| **An impermeable bladder (60) | |
| **A rigid wall (62) | |

\*= specific to only Embodiments 2 and 3
\*\*= specific to only Embodiment 3

With reference to FIGS. 1-11 and 14, several embodiments of the invention will be described. A first embodiment of the cell culture apparatus (20) of the present invention includes a vessel (22) having an internal chamber (24) suitable for the growth, in appropriate liquid media, of eukaryotic cells (99) in suspension or attached to the surface (26) of the chamber (24). The vessel (22) also includes a gas reservoir (28), a cell reservoir (30) for cells (99) of a pre-selected type suspended in a protective cryogenic media (32), and a media reservoir (34) for cell culture media (36) in which the cells are grown. The cell culture apparatus (20) is shaped to facilitate efficient packing in a cryogenic storage device and to be compatible both with automated retrieval from cryogenic storage and the object of growing cells in culture. For example, without limitation, the apparatus (20) may have a shape such as that of a conventional tissue culture flask, bottle or dish, or be especially formed in another shape or configuration as may be dictated by experiment design or objectives. The apparatus (20) will preferably occupy a volume in the range of about 10 milliliters to about 1 liter. Additionally, the apparatus may have a shape of a microtiter plate to hold different cell lines in the plurality of wells with specific growth media capable of studying the effect of stimuli (chemical, biological, irradiation or the like) when coupled with the detection/measuring device. It will be understood by one of ordinary skill in the art that various sizes, shapes and configurations may be employed in the cell culture apparatus (20), and that such variations in design are within the spirit and scope of the present invention.

Respecting the first embodiment of the present invention, the gas reservoir (28) may be disposed within chamber (24), or outside of it, and removably but sealingly connected with it by conventional means such as threads as shown in FIGS. 1-11. Gas reservoir (28) and chamber (24) are in fluid communication upon the removal of any seal (42), or upon opening of any valve (not shown), that closes reservoir (28). Wherever positioned, the gas reservoir is charged with a sterile compressed gas (38) of predetermined composition. The term "gas" as used herein refers to an expression of physical state as opposed to a statement of composition. A preferred predetermined composition of gas (38) for use in the present embodiment is substantially 95% air (78% nitrogen, 21% oxygen, 0.9% argon and 0.03% carbon dioxide) and 5% carbon dioxide ($CO_2$). That is, of every 100 molecules in a given volume approximately 74 will be nitrogen, 20 will be oxygen, 1 will be argon and 5 will be carbon dioxide. The gas reservoir is charged to a pressure determined by the relative volumes of the gas reservoir (28) and the chamber (24), and by the predetermined initial partial pressure of the component gases desired in the chamber (24) upon release of gas (38) from reservoir (28). After charging, the gas reservoir (28) is sealed from outside with a temperature or electrically sensitive primary seal, or with a temperature or electrically actuated valve, to retain the compressed gas (38). In addition to the primary gas reservoir seal, an optional safety seal may be applied temporarily and removed when the apparatus (20) is ready to be sealed for cryogenic storage.

In the first, second and third embodiments, described herein the cell culture (99) is composed of freshly prepared human peripheral blood lymphocytes, cells (99), which have been "immortalized" or virally transformed by Epstein-Barr virus (EBV) as is conventional, and maintained in RPMI 1640 media supplemented with 20% FBS. The cells (99) are pelleted by centrifugation as is conventional and resuspended in cryogenic protective media (32). Cryogenic protective media that have been used with various cells types include a DMSO-based medium and a Glycerol-based medium.

Cells are prepared for freezing at densities specific to that cell type, e.g., 1 milliliter of approximately 10 million cells per milliliter for LCLs or 1 milliliter of approximately 2-5 million cells per milliliter for fibroblasts.

An aliquot of cells (99) to be cultured resuspended in cryoprotective media (32) is placed into the cell reservoir (30) and frozen initially to at least minus 80° C. according to established protocols to maximize retained cell viability. The cell reservoir (30) may, optionally, be sealed with a temperature or electrically sensitive seal, or may comprise a capsule formed of low melting temperature water soluble nontoxic material such as, for example, a gelatin or similar material. It will be understood by one skilled in the art, that in some embodiments of the present invention, the use of a cell reservoir and/or the use of a media reservoir is optional. The volume of the aliquot, and therefore the number of cells, placed into the cell reservoir (30) is chosen to provide an initial cell culture density upon incubation in cell culture media (36) in the apparatus (20) of approximately 1 milliliter or approximately 10 million LCLs or 2-5 million fibroblasts. Thus, because the apparatus (20) may be manufactured in different sizes or volumes as required from one application to another, the volume of cryoprotective media (32) and cell culture media (36) utilized in the apparatus (20) will necessarily vary accordingly. However, the volume ratio of cell culture media (36) to cryoprotective media (32) is from approximately 4.0:1 to 15:1 in all embodiments.

It has been found that dilution of the cryoprotective media (32) by a factor of approximately 4.0-15 by cell culture media (36) to a final culture proportion of less than about 2% has negligible toxic effect on cell viability and growth.

An aliquot of cell culture media (36), RPMI 1640 media supplemented with 20% FBS, is placed into the media reservoir (34) and frozen initially to at least minus 80° C. The media reservoir (34) may, optionally, be sealed with a temperature or electrically sensitive seal. The volume of the aliquot, has described herein above is chosen to provide a predetermined initial cell density in culture upon combination of the cell culture media (36) with the protective cryogenic media (32) once the temperature of the apparatus has been raised above freezing temperature and the two media have changed to a liquid phase.

To facilitate manufacture and/or assembly of the apparatus (20) and/or charging of the apparatus (20) with any of the protective cryogenic media (32), cell culture media (36) or gas (38), the gas reservoir (28), cell reservoir (30) or the media reservoir (34) may be fabricated integrally to apparatus (20) or fabricated separately and affixed to the apparatus (20) either within or without chamber (24) by any suitable conventional means. In all cases respecting the presently first described embodiment however, and regardless of the method of fabrication, the gas reservoir (28), cell reservoir (30) and media reservoir (34) are in fluid communication with chamber (24) of apparatus (20) upon the opening of the seal or valve on any of reservoirs (28), (30) or (34). Similarly, in all cases respecting the described second and third embodiments however, and regardless of the method of fabrication, the gas reservoir (28) is in fluid communication with a gas space (52) of chamber (24) upon the opening of any seal (42), or valve (not shown) on gas reservoir (28); and cell reservoir (30) and media reservoir (34) are in fluid communication with a liquid space (54) of chamber (24) of apparatus (20) upon the opening of any seal or valve on any of reservoirs (30) or (34).

Figure 2:
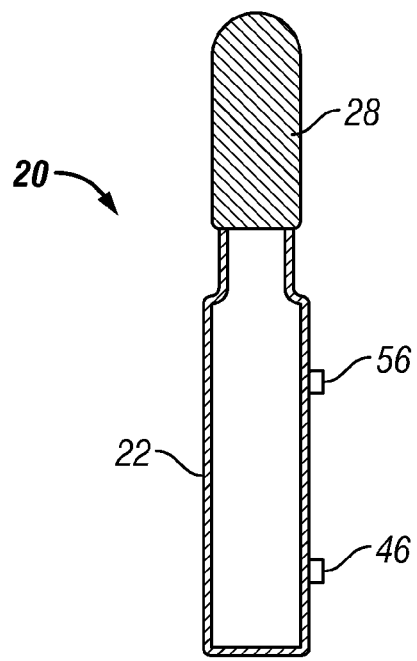
FIG. 2 is a side view of an embodiment of the present invention.
Figure 3:
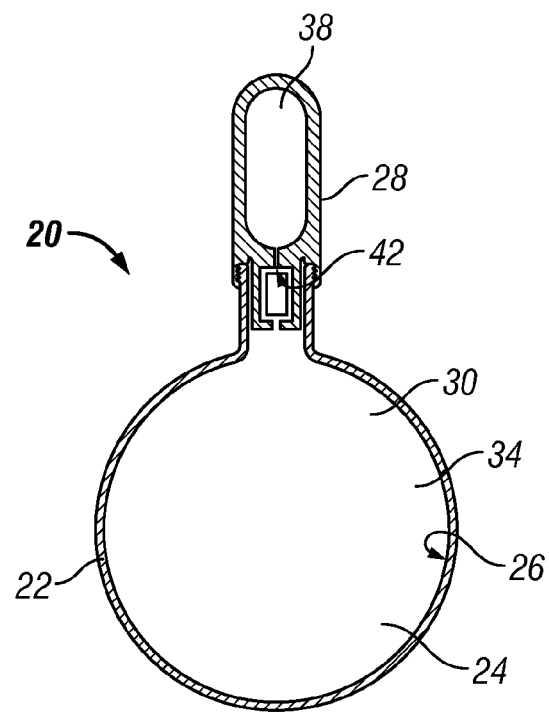
FIG. 3 is a cross-sectional view of the FIG. 1 embodiment, with addition of a gas-permeable, water-impermeable barrier to contain cells and medium in condition such zero gravity or turbulence caused by vehicular movement including acceleration.
Figure 4:
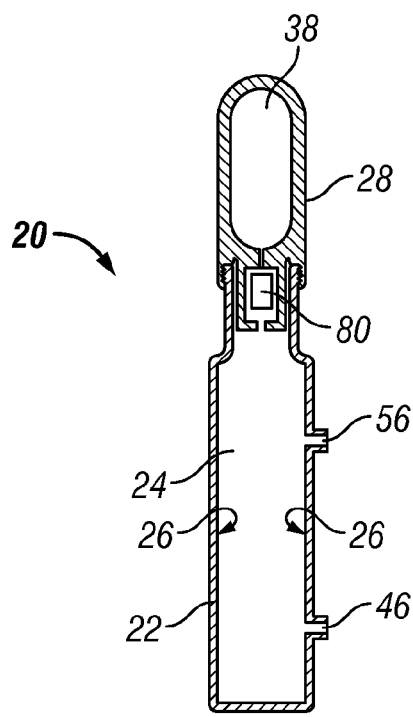
FIG. 4 is a cross-sectional view of the FIG. 2 embodiment.
Figure 5:
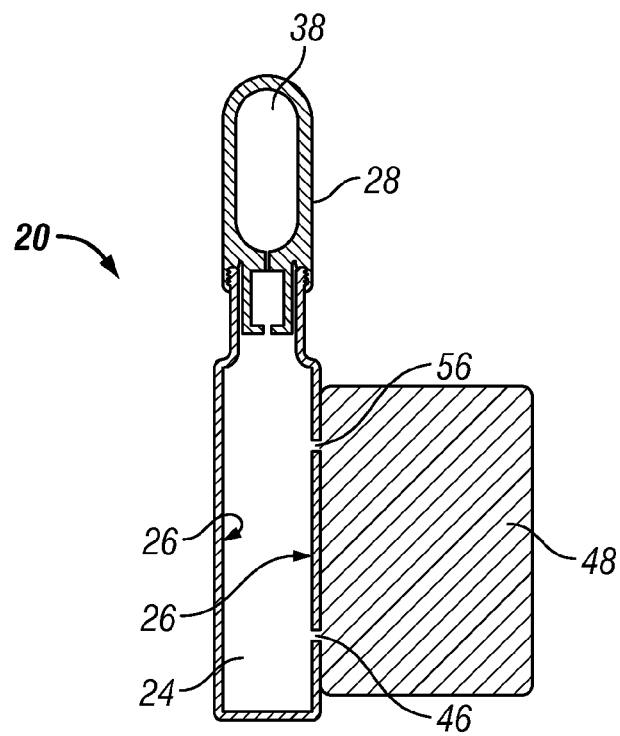
FIG. 5 is a cross-sectional view of the FIG. 2 embodiment interfaced with detection system/device.
Figure 6:
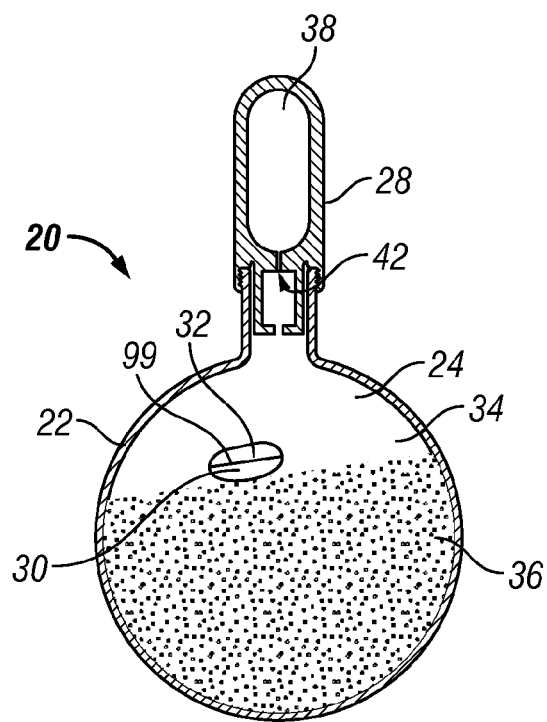
FIG. 6 is a cross-sectional view of the FIG. 1 embodiment containing cell culture media and cell culture in an example of a possible frozen for storage configuration.

In the described first embodiment, and with reference to FIGS. 2, 4 and 5, a port or channel (46) provides fluid communication between the interior of chamber (24) and a detecting or measuring instrument preferably integrated into a MEMS device (48) or other similar device such as, for example, a micro scale high performance liquid chromatography (HPLC) device and detector (NanoStream, Pasadena, Calif.). The MEMS device (48) intermittently, as programmed or commanded, withdraws small predetermined quantities (on the order of several microliters) of liquid media from chamber (24) through port (46) for analysis for preselected molecules and/or other parameters. Optionally, the MEMS device (48) may either be integrated with or affixed to apparatus (20), or the MEMS device (48) and apparatus (20) may be mated only after the apparatus has been selected for incubation. In a first embodiment of the present invention, a fluid connection via port or channel (46) is established between chamber (24) and MEMS device (48) or other measuring instrument which provides for sampling of the cell culture media and transfer to the measuring instrument.

Similarly, with reference to FIGS. 7-10, in a second and third embodiment of the present invention, a fluid connection via port or channel (46) is established between a liquid space (54) of chamber (24) and MEMS device (48) or other measuring instrument which provides for sampling of the cell culture media and transfer to the measuring instrument. In any embodiment of the present invention which is to be mated to an initially separate MEMS device (48), the port (46) of apparatus (20) is closed until after mating by a closure or seal such as, for example, a spring loaded ball valve or perforable diaphragm. In such embodiments, the structure of the MEMS device includes a member which operates the ball valve or which penetrates the diaphragm after the apparatus (20) and MEMS device (48) have been mated and a gastight seal has been where they join at port (40).

Figure 7A:
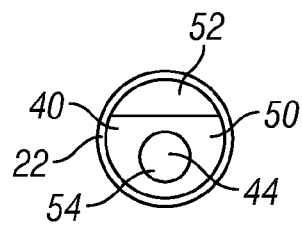
FIG. 7A is a cross-sectional view of an embodiment having a flexible partition separating gas space from liquid space.
Figure 7B:
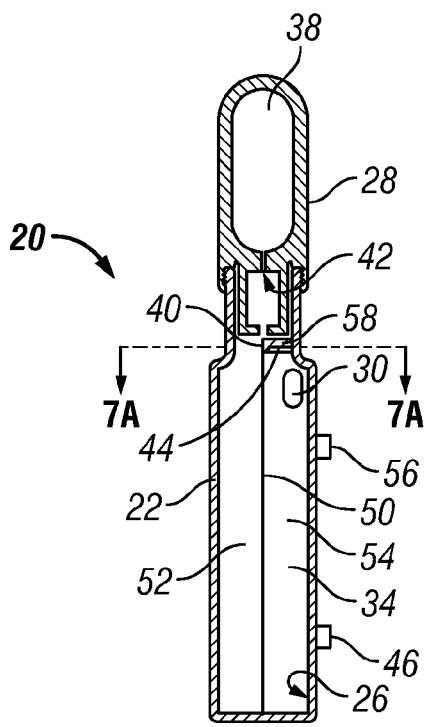
FIG. 7B is a cross-sectional view of the FIG. 7A embodiment taken along the plane 7B.

With reference to FIG. 7, a second embodiment of the present invention includes a gas permeable liquid impermeable flexible partition (50) sealed within chamber (24) and which forms two separate spaces, a gas space (52) and a liquid space (54), within chamber (24). The gas permeable liquid impermeable flexible partition (50) provides for exchange of gases between gas space (52) and liquid space (54) containing the cell culture (99). In this second embodiment, the gas reservoir (28) may be disposed within gas space (52) or outside it but in either case is in fluid communication with gas space (52) upon the removal of the seal closing gas reservoir (28), but is not in fluid communication with liquid space (54). In either location, the gas reservoir is charged with a sterile compressed gas (38) of predetermined composition and sealed with a temperature or electrically sensitive primary seal as described herein above.

With reference to FIGS. 7 and 7A, is shown partition wall (40), the edge of which flexible partition (50) is sealingly affixed. Liquid space access port (44) provides access to liquid space (54) during assembly and charging of the apparatus (20). Access port (44) is sealingly closed by access port closure (58). Access port closure (58) may be additionally maintained in position within access port (44) by the proximity of gas reservoir (28) upon final assembly of apparatus (20).

Figure 8:
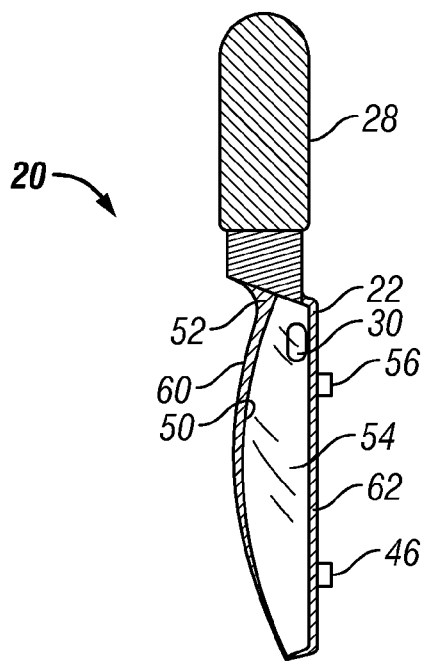
FIG. 8 is a side view of an embodiment having a flexible gas retention bladder lined by, e.g., a 0.22 μ to 0.45 μ filter in configuration for storage.
Figure 9:
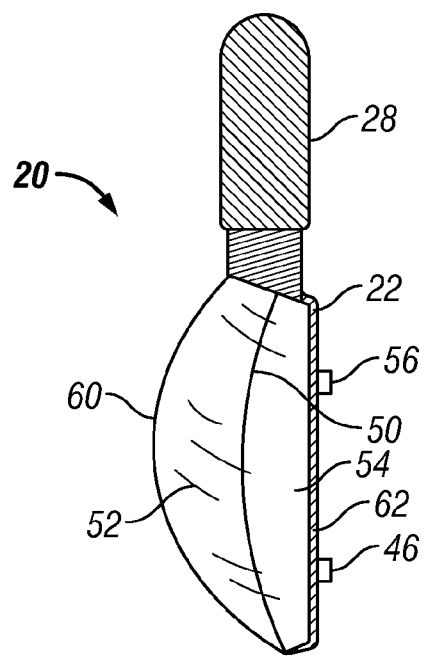
FIG. 9 is a side view of an embodiment having a flexible gas retention bladder in configuration for incubation and cell growth.
Figure 10:
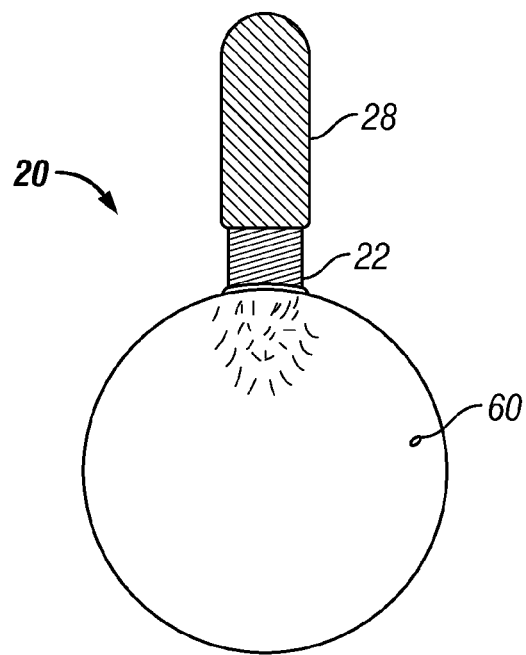
FIG. 10 is a top view of an embodiment having a flexible gas retention bladder in configuration for storage.
Figure 11A:
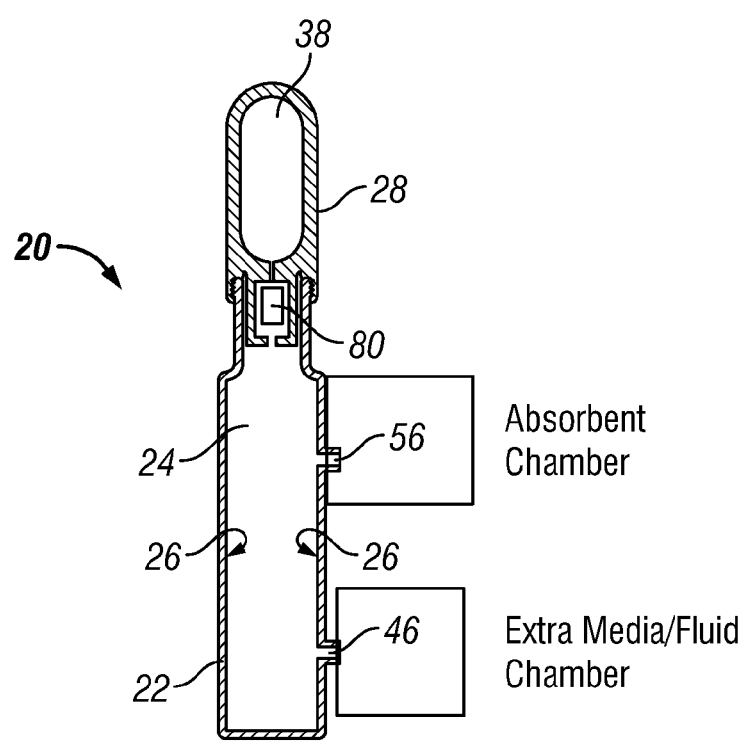
FIG. 11A is a cross-sectional view of an embodiment having an absorbent chamber and an extra media/fluid chamber.
Figure 11B:
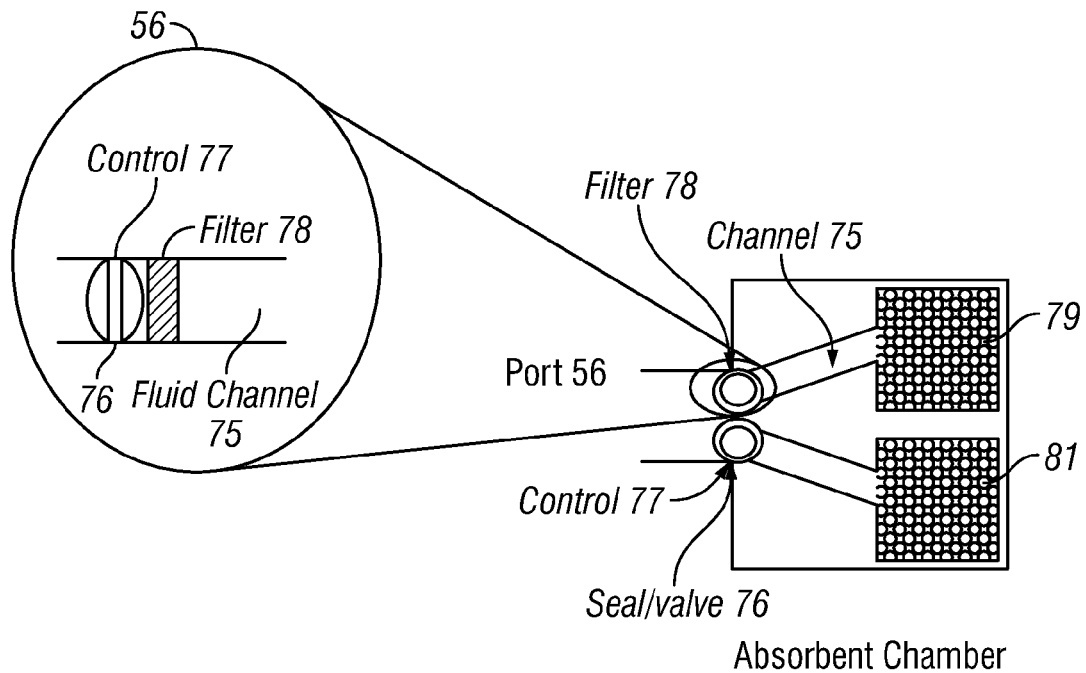
FIG. 11B is a detailed embodiment of the absorbent chamber.
Figure 11C:
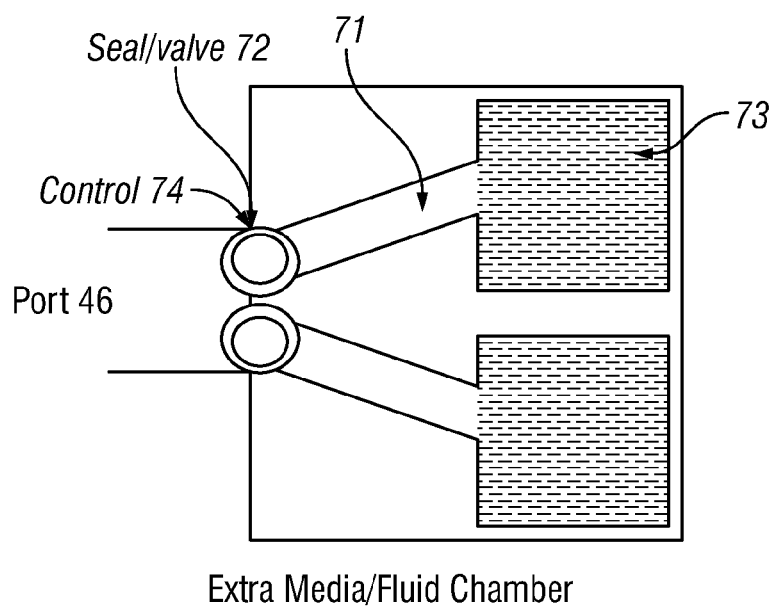
FIG. 11C is a detailed embodiment of the extra media/fluid chamber.
Figure 12A:
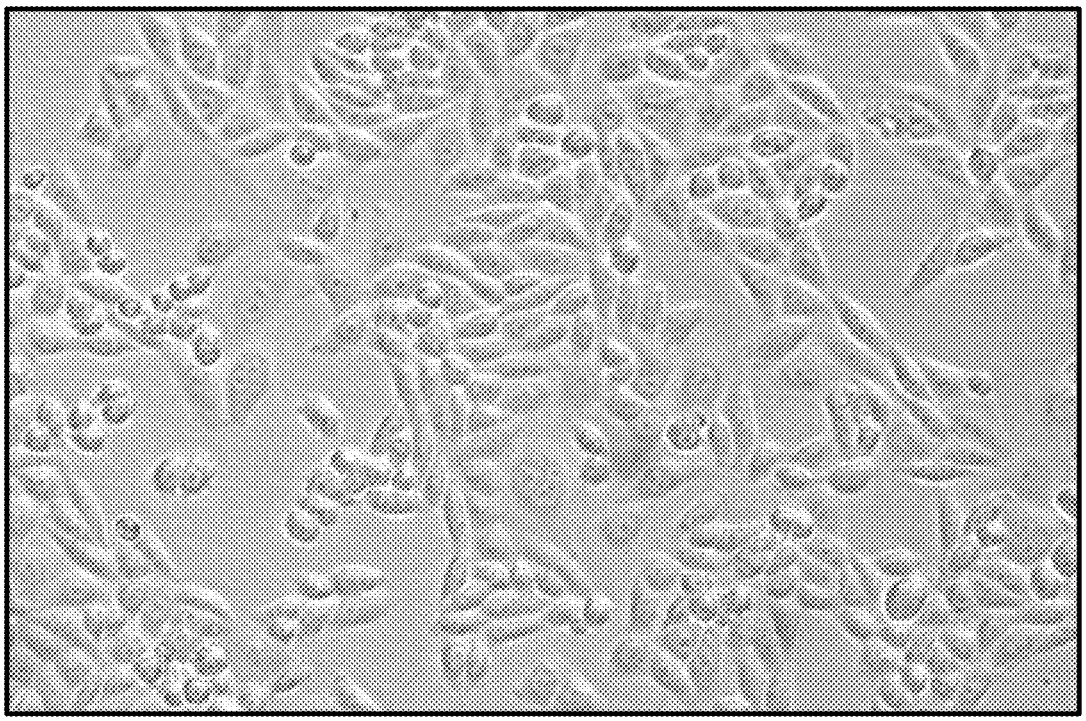
FIGS. 12A and 12B depicts cell culture after storage in a self-contained cell culture system.
Figure 12B:
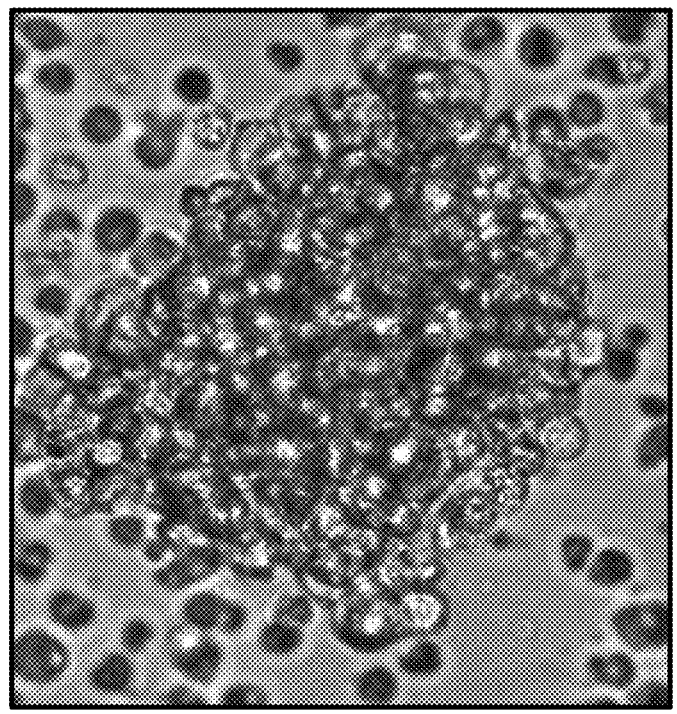

With reference to FIGS. 8-10, a third embodiment of the present invention includes a gas permeable liquid impermeable flexible partition (50) sealed within chamber (24), where sealed chamber (24) is formed between flexible gas and liquid impermeable bladder (60) and rigid wall (62) of vessel (22). In this third embodiment, the gas reservoir (28) may be disposed as described above with reference to the second embodiment of the present invention. The gas permeable liquid impermeable flexible partition (50) provides for exchange of gases between gas space (52) and liquid space (54) containing cell culture (99). With further reference to FIGS. 8 and 10, the third embodiment is shown in a noninflated condition as for freezing and storage. Upon thawing and incubation for cell culture, gas (38) is released from gas reservoir (28) to fill gas space (52), as shown in FIG. 9.

With respect to the present second and third embodiments, the cell reservoir (30) and the media reservoir (34) are in fluid communication with liquid space (54), but are not in fluid communication with gas space (52). The cell reservoir (30) and the media reservoir (34), respectively, are each filled and frozen as described herein above. It will be understood by one of ordinary skill in the art that chamber (24) or liquid space (54) may serve as media reservoir (34).

In the presently described second and third embodiments, port or channel (46) provides fluid communication between liquid space (54) and a measuring instrument integrated into a MEMS device (48) or other similar device as has been described herein above with respect to alternative embodiments. As will be clear from a reading of the entire disclosure herein, the second and third embodiments are especially well suited for cell culture in a microgravity environment as the volume of liquid space (54) under cell culture conditions at approximately 37° C. is approximately equal to the combined liquid volume of media (32, 36) thereby providing a substantially continuous liquid volume substantially free of gaseous voids, without the need for an imposed acceleration field.

Optionally, as is shown in FIGS. 2, 4, 5, 7-9, in any embodiment of the present invention, a second port or channel (56) adapted to mate sealingly with a corresponding port or channel of the MEMS device, as previously described with respect to port (46), may be formed in apparatus (20). Port or channel (56) is guarded by a 0.22 μ to 0.45 μ filter to serve as a barrier against cell culture contaminants such as bacterium or fungus. For example, in the described first, second or third embodiment of the present invention, the second port or channel (56) provides for fluid communication between chamber (24) and the MEMS device, while in the described second embodiment of the present invention, the second port or channel (56) provides for fluid communication between liquid space (54) and the MEMS device. Second port or channel (56) provides the option to introduce into chamber (24) or liquid space (54), respectively, pre-selected constituents stored within a MEMS device module. For example, constituents such as buffering agents or nutrients may be introduced via port or channel (56) in response to pH measurements made by a pH sensor. In addition, certain agents such a chemicals, toxins or growth factors under study, or other chemicals and drugs can be introduced via second port or channel (56) guarded by a filter to restrict the entry of cell culture contaminants.

EXAMPLES

Comparative Example 1

Conventional Cell Culture

Although conventional mammalian cell culture techniques are very convenient approaches, they require expertise and must be carried out under aseptic conditions. Contamination by common microorganisms such as bacteria and fungi is the major problem in mammalian cell culture. Therefore, mammalian cell culture cannot be established in a routine general-purpose biomedical laboratory; rather it is performed in a special, aseptic, designated work-area with proper instrumentation and limited traffic and personnel. Additionally, experienced hands are required to realize the system requirements and to minimize contamination. There are very specific requirements for the cell culture facility. Laminar flow hoods to reduce bacterial and fungal contamination are the most essential equipment required for cell culture, and all of the cell preparation steps are performed using these bully laminar flow hoods. The major advantage of working in a laminar flow environment is the protection from dust and microscopic contamination by a constant, stable flow of filtered air passing over the work surface. In addition sterilized handling, including gloves and an open flame, is very important to minimize the risk of contamination. A $CO_2$ incubator is the second most important equipment used in cell culture facilities, because it provides the optimum temperature, humidity and gas phase for the cell growth. A controlled atmosphere is achieved in a $CO_2$ incubator by circulating the gas over a humidifying tray and controlling the $CO_2$ tension with a $CO_2$ monitoring device.

The mammalian cells are preserved by freezing at −80° C. or preferably −140° C. or in liquid nitrogen. During cryopreservation, the cells are protected from cryoinjury by using glycerol or more commonly by using dimethylsulphoxide (DMSO). DMSO protects cells by reducing ice formation under subzero conditions. The cell suspension, preferably in high concentration, is cryopreserved in the presence of DMSO by the standard slow-freezing protocol at a rate of ~1° C. decrease per minute. Cells are maintained overnight at −80° C. and then are quickly transferred to either −140° C. or liquid nitrogen. The cells can be stored at this temperature for a long time or can be transported to different locations in dry ice by maintaining temperature at approximately −80° C. or lower. After receiving cells at the other location, cells are immediately transferred to −140° C. or liquid nitrogen.

When required, cells are recovered by rapid thawing, diluting slowly and seeding at high density. All of the steps are performed under aseptic conditions. Cells are quickly removed from the freezer and the container is thawed in a 37° C. water bath by carefully monitoring the thawing. As soon as the cells are thawed, the container is swabbed thoroughly with 70% alcohol, and is transferred into the laminar flow hood. Cells are carefully transferred drop wise into a 10 ml centrifuge tube containing Hanks balanced salt solution or phosphate buffered saline. This gradual dilution process is particularly important when DMSO is used as the cryoprotectant, with which sudden dilution can cause severe osmotic damage and reduce cell survival. The 10 ml tube containing cells is centrifuged at 230 g for 4:30 minutes. The DMSO in the supernatant is aspirated and the cells are recovered and transferred to the cell culture flask in the presence of pre-warmed growth medium. The cell culture flask is kept at 37° C. in a $CO_2$ incubator, and cell growth and viability are observed. All the steps are performed under strict aseptic conditions by experienced personnel to obtain the maximum viability and to reduce the risk of any contamination.

Example 2

Use of Vessel

A. Charging and Storage

In any order convenient, under aseptic and sterile conditions, the apparatus (20) is charged and stored as follows:

The apparatus (20) may be sealingly mated with a MEMS device module, HPLC or any other detection or measuring device.

The gas reservoir (28) is charged with gas (38) of a predetermined composition to a predetermined pressure. The gas reservoir (28) is sealed to retain the gas (38) with a removable seal such as a temperature sensitive plug designed to melt or to yield above a predetermined temperature, a diaphragm adapted to be penetrated, or a mechanically, thermally or electrically operated valve. The seal or valve may either be self-contained or connected to the MEMS device. The diaphragm or valve may be opened by conventional means such as by movement of a needle to penetrate the diaphragm or movement of a shaft to operate the valve that are connected to and actuated, for example, by the moveable core of an electrical solenoid, or by the expansion in response an increase in temperature from less than minus 80° C. to about 37° C. of a portion of the needle or valve shaft having a selected high coefficient of thermal expansion. In the case of the solenoid operated valve, the solenoid and electrical power supply may be contained on the MEMS device module.

The cell reservoir (30) is filled with a predetermined volume of protective cryogenic media (32) containing viable cells (99) of a selected cell type at a predetermined concentration as described herein.

The media reservoir (34) is filled with a predetermined volume of cell culture media (36).

Where the cell reservoir (30) and media reservoir (34) are integral to apparatus (20), reservoirs (30, 34) are first each charged as described then frozen to an initial temperature of minus 80° C. in the same freezing step according to established conventional protocols for cryopreservation of eukaryotic cells. Where the reservoirs (30, 34) are not integral to apparatus (20), each reservoir may be charged and frozen separately then affixed to apparatus (20) as described above. In either case, reservoirs (30, 34) may be sealed with a removable seal such as a temperature sensitive plug.

After reservoirs (28, 30, 34) have been charged, sealed and frozen as described, chamber (24) or spaces (52, 54) are purged of air by displacement by a relatively inert gas having a predetermined partial pressure of water vapor to minimize potential lyophilization, or in the alternative chamber (24) or spaces (52, 54) are evacuated of air. This purging should be accessed through port 46 and 56.

The apparatus (20) is then maintained at a temperature of less than about minus 100° C. (preferably minus about 140° C. or lower) by conventional means until selected for further use.

B. Cell Culture and Analysis

When desired for use and analysis the apparatus (20) is removed frozen from storage at less than about minus 100° C. and brought into thermal contact with an environment in which the temperature of the cell culture media (36) and the protective cryogenic media (32) containing cells (99) are brought to a temperature suitable for cell growth, such as 37° C., or other predetermined temperature, according to established protocols as is conventional.

Upon increase in temperature of apparatus (20) to above a predetermined temperature in the range of approximately 25° C. to 37° C. the temperature suitable for cell growth, for example, sensitive seals closing cell reservoir (30) and media reservoir (34) melt or otherwise open to release their contents.

Upon increase in temperature of apparatus (20) to above a predetermined temperature in the range of approximately 25° C. to 37° C. a temperature sensitive seal closing gas reservoir (28) melts or otherwise opens as is conventional, or alternatively by conventional means such as, the expansion of an expansion member penetrates a diaphragm seal (42), or alternatively, operates a ball and socket valve (not shown), on gas reservoir (28) to release gas (38) as described herein. With reference to FIG. 4, such conventional means for opening gas reservoir (28) are depicted by the stylized device (80). For clarity, device (80) is not shown in FIGS. 3, 5, 6 and 7.

Preferably, the combination of cell culture media (36) and the protective cryogenic media (32) accomplishes a dilution of the cryoprotectant to a final concentration having minimal effect on cell viability and growth, and suspends the cells (99) in the cell culture media. Optionally, mixing of the two liquid media aliquots may be further accomplished such as by a brief rotation of apparatus (20) or brief gentle agitation as by a magnetic stirring bar placed in the media for example.

In the first described embodiment of apparatus (20), when in a microgravity environment, the apparatus (20) is placed in a slowly rotating structure to impose a small acceleration field which settles the liquid media into a substantially continuous volume which contacts the gas phase but which is substantially free of gaseous voids in the liquid phase.

In the case of the second and third embodiments of the present invention, release of gas (38) into gas space (52) causes flexible partition (50) to move in response to gas pressure so as to cause liquid space (54) to conform approximately to the combined volume of the cell culture, media (36) and the protective cryogenic media (32) in liquid space (54). Since the liquid culture media is contained within a liquid space (54) approximately equal to its own volume, the liquid media will be substantially free of gaseous voids in a microgravity environment and cell culture may therefore be maintained without the imposition of an acceleration field.

Example 3

Effect of Cryoprotectant on Cell Viability

Cryoprotectant can be left in the cell growth media and cell viability can be maintained in culture by a simple dilution of the cells with growth media (this is compared to the conventional method of removing the cryoprotectant upon cell revival).

Mammalian cells/tissue can be cryopreserved for a longer durations under subzero conditions in the presence of cryoprotectant such as DMSO or glycerol. The final concentration of DMSO is maintained at 7.5% in the cell suspension in the growth medium. In order to revive cells again the cryoprotectant can be diluted 5-10 times with the growth media to overcome toxic effect of DMSO.

The self-contained cell culture system was tested on various human as well as non-human cell lines such as lymphoblastoid cells, fibroblasts, a lung carcinoma cell line and a Chinese hamster ovary cell line. We were able to obtain cell viability and growth in all these cell lines. In order to test cell survival for extended periods of cryopreservation, lymphoblastoid cell lines were preserved at −140° C. Every month one self-contained system was thawed at 37° C. to revive cryopreserved cells. Cells were clumped together and the pH of media changed from 7.4 to 7.0 after 2 days indicating cell growth. In addition, 40-50% cell viability was observed by using 0.4% Tryphan blue dye that stains dead cells. These cells were successfully revived at 19 months of cryopreservation in the self-contained system, establishing that cells can be cryopreserved at least that long; we continue to remove cells frozen more than 19 months ago to determine if there is a limit on cryopreservation time. Similarly fibroblasts, Chinese hamster ovary cells, lung carcinoma cells were successfully revived and the culture was confluent in 4-5 days.

Example 4

Effect of Temperature Fluctuation on Cells

Mammalian cells were observed to tolerate storage temperature raise from liquid nitrogen to −140° C. to low cost −20° C. to maintain sufficient viability for subsequent culturing (mammalian cells were known in published literature to deteriorate rapidly if the temperature rises above −50° C.).

The cells can tolerate temperature fluctuation can enable the transportation of cells at −20° C., thereby eliminating the requirement of dry ice for shipment. However, some specialized cells such as stem cells cannot tolerate temperature fluctuation from −80° C. to −20° C.

Storage at −80° C.: Lymphoblastoid cells stored originally at −140° C. were moved to −80° C. for at least a week and then stored back at −140° C. Cell revival was not altered compared to control cells stored at −140° C. without interruption. This data indicate that cell viability would not be affected when cells would be transported at the temperature of dry ice.

Storage at −20° C.: To demonstrate further the ability to transport cells at −20° C. without the need for dry ice, we preserved lymphoblastoid cells and lung carcinoma cells at −20° C. These cell lines were originally stored at −140° C. for nearly one year. The cells were revived in the self-contained system after 1, 2, 3 and 4 days of storage at −20° C. We observed successful growth in these containers; however, the cell viability decreased with longer storage at −20° C. and it varied among different cell lines. For example, lymphoblastoid cells could be stored up to 3 days at −20° C., while lung carcinoma cells were able to be revived and grown beyond 5 days of −20° C. storage.

Example 5

Prototype of Completely Closed Cell Culture System

We have used 25 cm$^2$ and 75cm$^2$ tissue culture flasks for these experiments. Initially, 5-15 ml of growth media was frozen inside a tissue culture flask. Separately, cells were frozen in a cryoprotectant media containing 7.5% DMSO or 15-20% glycerol in 1 ml cryogenic storage tubes. After both the media and cell sample were frozen, the cryogenic tube was placed, opened, in the frozen media flask, and the flask was flushed with a mixture of air (95%) and $CO_2$ (5%) using a pressurized gas tank. Immediately, the flask was sealed and placed in a −140° C. freezer. At periodic time intervals, a flask was removed from the freezer and allowed to thaw in an incubator.

Example 6

Chips Manufactured at CalTech

Figure 13A:
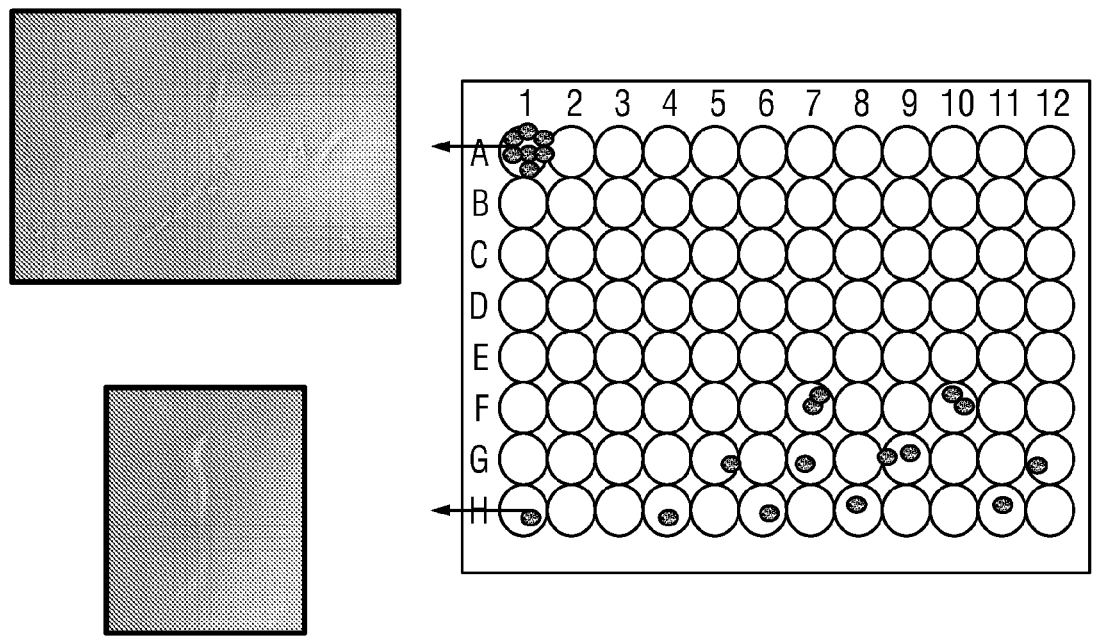
FIG. 13A depicts single cell cryopreservation of fibroblasts on 96 wells plate.
Figure 13B:
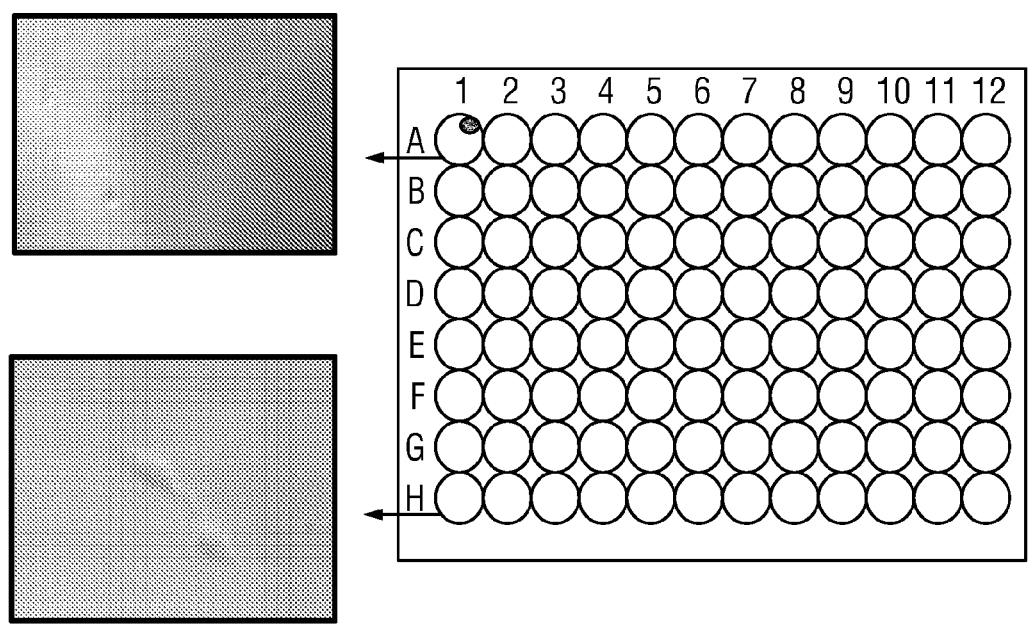
FIG. 13B depicts single cell cryopreservation of lung carcinoma cells on 96 wells plate.
Figure 14:
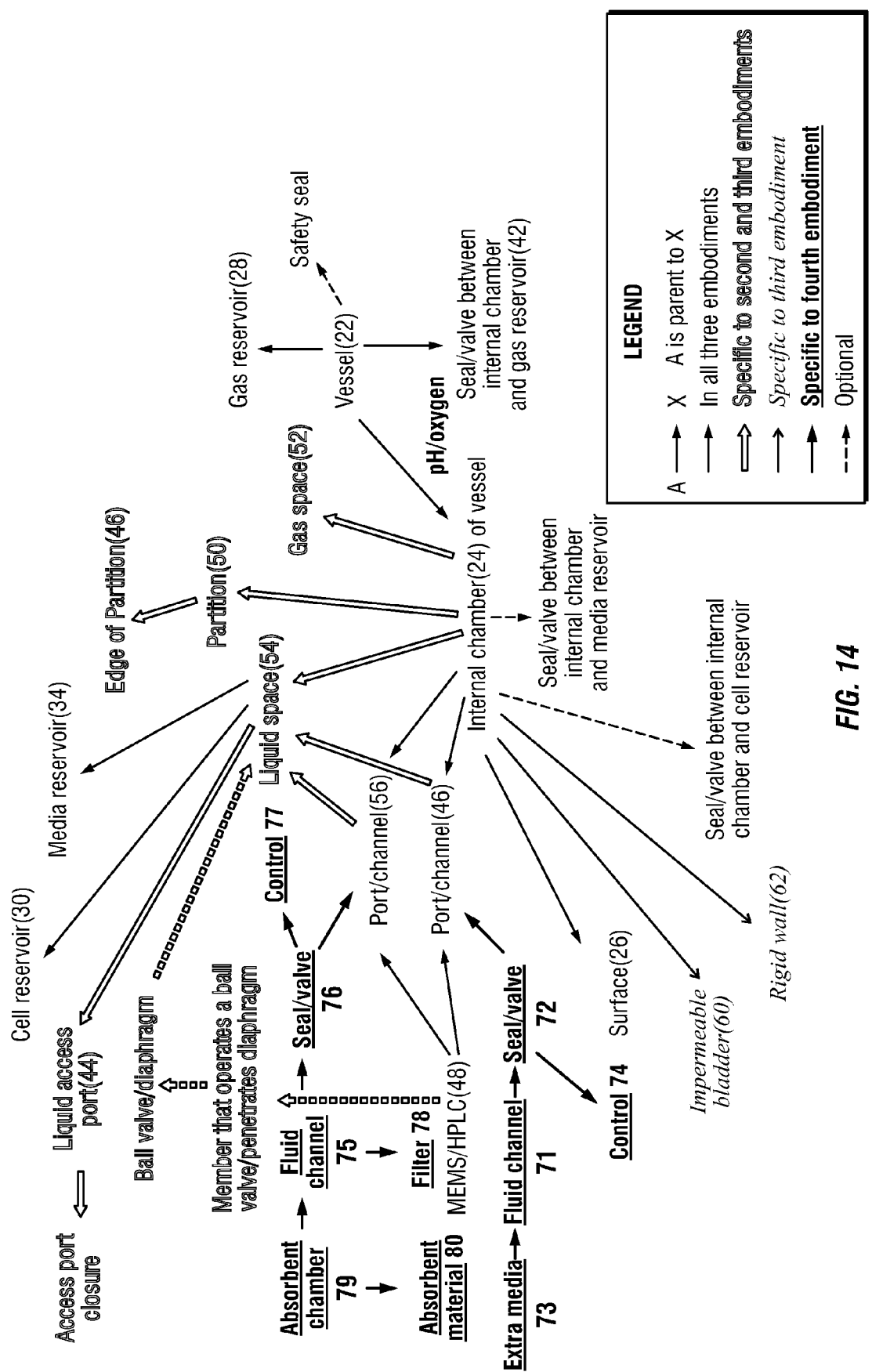
FIG. 14 is a graphical depiction of 3 embodiments of the inventive vessel.

Caltech is manufacturing 1 cm×1 cm parylene/$SiO_2$ chips with variable size cell enclosures ranging from 25-100 microns in width and 500 microns in depth. We were able to grow successfully cells on these chips. In order to demonstrate single cell revival on these chips, we cryopreserved mammalian cells (lymphoblastoid cells, lung carcinoma cells and fibroblasts) in 96 well plates. We were able to revive cryopreserved single cells and show that the revived individual cells were capable of growing and dividing as shown in FIGS. 13a-13b.

Example 7

Description of Components of a Self-Contained Cell Culture Device

The self-contained cell culture apparatus of a fourth embodiment described earlier is a multi-compartment device. It has three fundamental categories of compartments: 1). A main compartment for the cultured specimen, 2) multiple compartments for extra media and gases to add or replace media and gases in the main compartment when needed, valved from the main and can be opened by a control 3) multiple absorbent compartments to remove media and/or gases, separated from the main compartment by a membrane that can be opened or closed by activation of a control. The membranes are further separated from the absorbent chamber by filters that block the passage of cell specimen from the main chamber to the absorbent chambers. In some implementation, such as using micromachined-based valves and microchannels for filter, the function of the membrane and filter can be integrated into one.

The main compartment contains the media and gases necessary for cryopreservation, storage, transportation, distribution and culturing of cells and tissue consistent with the self-contained process described in this disclosure. The main compartment can also include in situ sensors. These sensors can be used to monitor the self-contained culture system. Examples of parameters to be monitored are oxygen and pH. Oxygen level can be monitored using a fluorescence technique based on a ruthenium complex. The ruthenium complex can be encapsulated in a silica matrix (sol-gel technology) or it can be immobilized in a polymer, both materials should be optically transparent so that fluorescence can be detected. For a single use oxygen measurement, one can use the calorimetric indigo carmine method (ASTM D888-03). The reduced form of indigo carmine, which is colorless, reacts with dissolved oxygen to form a blue product, but this process is essentially irreversible unless electrochemistry is available.

Example 8

Depiction of Fourth Embodiment

More particularly, in a fourth embodiment of the self-contained culture apparatus, methods of providing material to remove degrading culture media that can compromise the cell viability is provided, as well as additional chambers of media and gases as replacement. In this fourth embodiment the valve (42) on the Gas Reservoir (28) is regulated for the amount of gas released and is designed for multiple opening and closing. This will enable gases to be injected into the culture media at a regular interval in order to increase the duration of cell viability. Whereas port (46) is optional in embodiment one, two and three, on this fourth embodiment, there will be at least one available port (46) on the Internal Chamber (24) or Liquid Space (54). One of these ports (46) will be connected a Fluid Channel (71) that multiplex into at least one additional Media Chamber (73), gated by a seal or valve (72), which can be released by control (74) at a regular time or at the time when new media is needed to increase the duration of cell viability in the Internal Chamber (24). Whereas port (56) is optional in embodiment one, two and three, on this fourth embodiment, there will be at least one available port (56) on the Internal Chamber (24) or Liquid Space (54). One of these ports (56) will be connected to a Fluid Channel (75), which multiplex into at least one additional Absorbent Chamber (79). Each Absorbent Chamber (79) is normally closed by a seal or valve (76), then can be opened by a control (77). Between the Absorbent Chamber (79) and the seal (76) is a device or material that function as a Cell Filter (78), which permits the flow of fluid, but not cells. Within the Absorbent Chamber (79), an absorbent material (81) will have the function of extracting the fluid and gases from the Internal Chamber (24). The absorber material must have the ability to extract fluid entirely, including the ions and macromolecules within. One example of a passive, biocompatible and aseptic "sponge" to soak up media is a hydrogel based on cellulose derivatives. The hydrogel is a superabsorbant and has been used to absorb body water from edemas as well as synthetic urine. The hydrogel is synthesized from carboxymethylcellulose and hydroxyethylcellulose, cross-linked with divinylsulphone. A. Sannino, A. Esposito, A. De Rosa, A. Cozzolino, L. Ambrosio, L. Nicolais, "Biomedical Application of a Superabsorbent Hydrogel for Body Water Elimination in the Treatment of Edemas", Journal of Biomedical Materials Research Part A, Vol. 67A, pp. 1016-1024 (2003); A. Sannino, G. Mensitieri, L. Nicolais, "Water and Synthetic Urine Sorption Capacity of Cellulose-Based Hydrogels under a Compressive Stress Field", Journal of Applied Polymer Science, Vol. 91, pp. 3791-3796 (2004).

Optionally, in this fourth embodiment, sensors can be integrated to monitor relevant culture parameters such as pH and $O_2$ level. Oxygen level can be monitored using a fluorescence technique based on a ruthenium complex. The ruthenium complex can be encapsulated in a silica matrix (sol-gel technology) or it can be immobilized in a polymer, both materials should be optically transparent so that fluorescence can be detected. For a single use oxygen measurement, one can use the colorimetric indigo carmine method (ASTM D888-03). The reduced form of indigo carmine, which is colorless, reacts with dissolved oxygen to form a blue product, but this process is essentially irreversible unless electrochemistry is available.

The dye Phenol Red is commonly found in cell culture media to monitor pH. However, its sensitivity is minimal and therefore typically serves as an indicator for failure of the culture. More sensitive techniques now exist. An example of continuous pH monitoring can be done using a pH sensitive dye such as 1-hydroxypyrene-3,5,7-sufonic acid (HPTS), with a pKa=7.2. This dye would also be detected using fluorescence. For a visual calorimetric pH sensor, one can use bromothymol blue, another pH indicator. Bromothymol blue, also known as bromthymol blue, is a chemical indicator for weak acids and bases. Following are given its colors at different solution pH values. This indicator dye is also reversible, but is less sensitive than HPTS.

Alkaline (basic)–Blue (pH>7)
Neutral–Green (pH=7)
Acid–Yellow (pH<7)

For both the oxygen and pH indicator aye, there are two preferred ways of incorporating them into the fourth embodiment. In one preferred embodiment, the dyes can be immobilized in materials that are used to construct the Internal Chamber (22), which will have the properties of an optically transparent polymer. Another preferred method of incorporation is dissolving the dye into the culture media.

Various pH sensors are known in the art and are discussed in references such as Y. Kostov, P. Harms, L. Randers-Eichhorn, G. Rao, "Low-Cost Microbioreactor for High-Throughput Bioprocessing", Biotechnology and Bioengineering, Vol. 72, pp. 346-352 (2001); B. H. Weigl, A. Holobar, W. Treetnak, I. Klimant, H. Kraus, P. O'Leary, O. S. Wolfbeis, "Optical Triple Sensor for Measuring pH, Oxygen and Carbon Dioxide", Journal of Biotechnology, Vol.32, pp. 127-138 (1994); F. W. Chaplen, W. E. Fahl and D. C. Cameron, "Method for determination of free intracellular and extracellular methyglyoxal in animal cells grown in culture. Anal Biochem. 1996 238(2):171-8; and B. Jovov, N. K. Wills, S. A. Lewis, "A spectroscopic method for assessing confluence of eptithelial cell cultures", Am J Physiol. 1991 261(6) C1196-203.

While the present invention has been described in connection with what is presently considered to be the most practical and preferred embodiments, it is to be understood that the invention is not to be limited to the disclosed embodiments, but to the contrary, is intended to cover various modifications and equivalent arrangements included within the spirit of the invention, which are set forth in the appended claims, and which scope is to be accorded the broadest interpretation so as to encompass all such modifications and equivalent structures.

What is claimed is:

1. A kit comprising
a self-contained cell culture vessel comprising a cell reservoir, a media reservoir distinct from the cell reservoir, and a gas reservoir;
cells and a cryoprotectant containing medium disposed in said cell reservoir;
a liquid cell culture medium disposed in said media reservoir in an amount capable of diluting the cryoprotectant to a volume suitable for cell growth, wherein thawing of the cryoprotectant containing medium and the liquid cell culture medium combines the cells, the cryoprotectant containing medium, and the liquid cell culture medium to provide a medium to culture the cells; and
gas disposed in the gas reservoir.

2. The kit of claim 1 maintained at a subzero temperature.

3. The kit of claim 1, further comprising an internal chamber.

4. The kit of claim 3, wherein
the internal chamber defines a space therein and has an internal surface;
the internal chamber defines at least one optionally sealable port or channel;
the internal chamber defines at least one sealable opening for receiving a gas reservoir capable of fluid communication with the internal chamber;
wherein the gas reservoir contains a valve or removable seal;
wherein the cell reservoir is capable of fluid communication with the internal chamber and defines an optional valve or seal therebetween;
wherein the media reservoir is capable of fluid communication with the internal chamber and defines an optional valve or seal therebetween;
wherein the vessel is capable of being sealed; and
wherein the vessel is made from a material capable of withstanding subzero temperatures without degrading.

5. The kit of claim 4 wherein the vessel further comprises a liquid impermeable flexible partition having two sides displaced within the internal chamber, the two sides defining a first and a second space within the internal chamber;
wherein the partition is capable of exchanging gas between said first and second space;
wherein the first space is capable of containing a liquid in communication with at least one port or channel, and defines a sealable access port, and
wherein the first space is capable of fluid communication with the cell reservoir and/or the media reservoir;
wherein the second space is capable of containing a gas, and said second space is capable of fluid communication with the gas reservoir; and
wherein the edges of the partition are sealed to a portion of the internal surface of the internal chamber to prevent liquid communication between said spaces.

6. The kit of claim 5, wherein the second space for containing a gas is further defined by
a fluid and gas impermeable expandable wall affixed to a rigid wall of the internal chamber and forming an integral portion of the internal chamber.

7. The kit of claim 4
wherein one or more of the valves or seals is capable of opening and closing;
wherein at least one port or channel sealably connects to at least one additional media chamber through at least one fluid channel, wherein at least one valve or seal is displaced between each port or channel and each media chamber; and wherein the media chamber is located externally to the vessel;
wherein at least one port or channel sealably connects to at least one absorbent chamber, wherein at least one valve or seal is displaced between each additional port or channel and the absorbent chamber; and
further comprising a cell filter between each valve or seal and each absorbent chamber.

8. The kit of claim 3,
wherein the gas reservoir is a self-contained capsule disposed within the internal chamber.

9. The kit of claim 3,
wherein the gas reservoir is disposed outside the internal chamber, and is sealably connected to the internal chamber.
10. The kit of claim 3,
wherein the cell reservoir and the media reservoir are contained within the internal chamber.
11. The kit of claim 3,
wherein the cell reservoir and/or the media reservoir is a self-contained capsule.
12. The kit of claim 4,
wherein the seal or valve defined between the gas reservoir and the internal chamber is selected from the group consisting of a) a temperature or electrically sensitive seal; b) a diaphragm adapted to be penetrated, or c) a mechanically, thermally or electrically operated valve.
13. The kit of claim 12,
comprising a temperature sensitive seal and further comprising a safety seal.
14. The kit of claim 4,
wherein the internal chamber is removably or fixedly connected to at least one measuring device via at least one port or channel.
15. The kit of claim 14,
wherein the measuring device is a Micro Electro Mechanical System (MEMS) and/or high performance liquid chromatograph (HPLC).
16. The kit of claim 14,
wherein a port or channel defines a mechanism to provide fluid communication between the internal chamber and the measuring device.
17. The kit of claim 16,
wherein the mechanism is a ball valve or a perforable diaphragm.
18. The kit of claim 4,
wherein the internal chamber defines one or two ports or channels.
19. The kit of claim 17,
wherein the measuring device further comprises a member for operating the ball valve or for penetrating the diaphragm.
20. The kit of claim 14, further comprising
a filter within the port or channel for preventing contamination in the internal chamber.
21. The kit of claim 4,
wherein the sealable access port is removably sealed with an access port closure.
22. The kit of claim 4, further comprising
at least one sensor externally connected to at least one port or channel or disposed inside the internal chamber.
23. The kit of claim 22,
wherein the sensor senses oxygen, $CO_2$, or pH levels.

* * * * *

UNITED STATES PATENT AND TRADEMARK OFFICE
CERTIFICATE OF CORRECTION

PATENT NO. : 7,691,626 B2 Page 1 of 1
APPLICATION NO. : 10/579952
DATED : April 6, 2010
INVENTOR(S) : Edward R. B. McCabe et al.

It is certified that error appears in the above-identified patent and that said Letters Patent is hereby corrected as shown below:

In the Specification, at column 1, please delete the paragraph beginning at line 17:

"The U.S. Government has a paid-up license in this invention and the right in limited circumstances to require the patent owner to license others on reasonable terms as provided for by the terms of Contract/Grant No. NCC2-1364 awarded by the Center for Cell Mimetic Space Exploration (CMISE)."

and replace with:

--This invention was made with Government support of Grant No. NCC2-1364 awarded by NASA. The Government has certain rights in this invention.--

Signed and Sealed this

First Day of June, 2010

David J. Kappos
*Director of the United States Patent and Trademark Office*